(12) United States Patent
Du et al.

(10) Patent No.: US 9,126,937 B2
(45) Date of Patent: Sep. 8, 2015

(54) ALKYLATED IMINO SUGARS EXHIBITING GLUCOSIDASE INHIBITION AND THEIR METHOD OF USE

(71) Applicants: Baruch S. Blumberg Institute, Doylestown, PA (US); Philadelphia Health & Education Corporation, Philadelphia, PA (US)

(72) Inventors: Yanming Du, Cheshire, CT (US); Xiaodong Xu, Doylestown, PA (US); Hong Ye, Lansdale, PA (US); Jinhong Chang, Chalfont, PA (US); Timothy M. Block, Doylestown, PA (US)

(73) Assignees: Baruch S. Blumberg Institute, Doylestown, PA (US); Drexel University, Philadelphia, PA (US)

( * ) Notice: Subject to any disclaimer, the term of this patent is extended or adjusted under 35 U.S.C. 154(b) by 0 days.

(21) Appl. No.: 14/388,175

(22) PCT Filed: Mar. 27, 2013

(86) PCT No.: PCT/US2013/034033
§ 371 (c)(1),
(2) Date: Sep. 25, 2014

(87) PCT Pub. No.: WO2013/148791
PCT Pub. Date: Oct. 3, 2013

(65) Prior Publication Data
US 2015/0119366 A1    Apr. 30, 2015

Related U.S. Application Data

(60) Provisional application No. 61/616,753, filed on Mar. 28, 2012.

(51) Int. Cl.
| | |
|---|---|
| C07D 211/40 | (2006.01) |
| A61K 31/445 | (2006.01) |
| C07D 211/46 | (2006.01) |
| C07D 413/06 | (2006.01) |
| C07F 9/59 | (2006.01) |

(52) U.S. Cl.
CPC ............ *C07D 211/46* (2013.01); *C07D 413/06* (2013.01); *C07F 9/591* (2013.01)

(58) Field of Classification Search
CPC ...................................................... C07D 211/88
USPC .................................. 546/219, 220; 514/328
See application file for complete search history.

(56) References Cited

U.S. PATENT DOCUMENTS

| | | |
|---|---|---|
| 2006/0111400 A1 | 5/2006 | Ali |
| 2011/0065754 A1 | 3/2011 | Ramstedt |
| 2011/0189771 A1 | 8/2011 | Block et al. |

FOREIGN PATENT DOCUMENTS

| JP | 56103163 | * 8/1981 |
|---|---|---|

OTHER PUBLICATIONS

Greimel et al Bioorganic and Medicinal Chemistry Letters 2006, 16, 2067-2070.*
Greimel et al, Bioorganic and Medicinal Chemistry Letters, 2006, 16, 2067-2070.

* cited by examiner

*Primary Examiner* — John Mabry
(74) *Attorney, Agent, or Firm* — Joseph F. Aceto, Esq.

(57) ABSTRACT

Pharmaceutical compositions of the invention comprise alkylated imino sugars derivatives having a disease-modifying action in the treatment of diseases associated with glucosidase activity that include Viral hemorrhagic fevers, and any other diseases involving glucosidase activity.

7 Claims, No Drawings

US 9,126,937 B2

ALKYLATED IMINO SUGARS EXHIBITING GLUCOSIDASE INHIBITION AND THEIR METHOD OF USE

STATEMENT OF FEDERALLY FUNDED RESEARCH

This invention was made with Government support under HDTRA1-10-C-0068 awarded by the Defense Threat Reduction Agency. The Government has certain rights in the invention.

CROSS-REFERENCE TO RELATED APPLICATIONS

This application is a U.S. National Phase of International Application No. PCT/US2013/034033, filed on Mar. 27, 2013 which claims the benefit of U.S. Provisional Application No. 61/616,753 filed Mar. 28, 2012, now expired which is herein incorporated by reference in their entirety.

FIELD OF INVENTION

The present invention describes compounds and methods useful as glucosidase inhibitors, useful as anti-viral agents for the treatment of viral hemorrhagic fevers and related conditions. The present invention further describes a novel chemotype useful for the treatment of viral infection and other diseases that involve glucosidase activity.

BACKGROUND OF THE INVENTION

Viral hemorrhagic fevers (VHFs) refer to severe multisystem syndrome, caused by viruses of four distinct families: arenaviruses, filoviruses, bunyaviruses, and flaviviruses. These symptoms are often accompanied by hemorrhage (bleeding). While some types of hemorrhagic fever viruses can cause relatively mild illnesses, many of these viruses cause severe, life-threatening disease. Currently, there is no treatment or established cure for VHF infection. Ribavirin, an antiviral drug, has been effective in treating some individuals with Lassa fever or hemorrhagic fever with renal syndrome (HFRS). Treatment with convalescent-phase plasma has been used with success in some patients with Argentine hemorrhagic fever.

In the search for new anti VHF viruses, researchers have tried using nucleosides as inhibitors of dengue virus (Zheng Yin, et al, PNAS 2009, 20435-20439), kinase inhibitors for inhibition of Lassa virus and Ebola virus infection (Andrey Kobokoltsov, Arch Virol 2012, 121-127), acridone derivatives as inhibitors of Junin virus RNA synthesis (Claudia Sepulveda, Antiviral Res. 2012, 16-22). However, these approaches have met with limited success. Thus, there is a long felt need for new antiviral drugs that are both disease-modifying and effective in treating patients that are infected viral hemorrhagic fever (VHFs) viruses.

One approach to developing antiviral compounds is to design a molecule targeting host factors that are essential for the virus life cycle, thereby providing antiviral effect. In theory, by targeting host pathways used in common by all the hemorrhagic fever viruses, it should be possible to discover broad spectrum antiviral agents. If the viruses are more dependent upon the host pathway than is the host, selectivity and a useful therapeutic is possible. Viral hemorrhagic fevers (VHF) viruses each contain different RNA genomes, but they are all enveloped with glycosylated viral proteins and share a similar morphogenesis strategy of budding, which would make them sensitive to glucosidase inhibitors. This is presumably because the folding of N-linked glycoproteins in these viruses depends upon calnexin, a chaperon that folds proteins that have been trimmed by the Endoplasmic reticulum (ER) glucosidase. Most cell functions can compensate for a reduction in glucosidase enzyme function; however, the calnexin dependent viral envelope proteins cannot apparently use alternative processing pathways. Thus, glucosidase inhibitors would be selective antiviral agents against multiple enveloped viruses.

Imino sugars, such as deoxynojirimycin (DNJ) and its derivatives have been found glucosidase inhibitors. Despite great potential as broad-spectrum antivirals, clinical development of imino sugars has been limited by their low efficacy. The glucosidase inhibitors, N-butyl-DNJ (NBDNJ) currently approved by the US and European FDAs for use in the management of Gaucher's disease and Cellgosovir (in Phase II human trials for Hepatitis C virus infection), both require near millimolar concentrations to achieve $EC_{50}$ values in tissue culture against their target viruses. NBDNJ has been dropped for antiviral development, due to the failure to achieve therapeutic concentration in vivo. Thus, there remains an urgent and unmet need for glucosidase inhibitors useful as antiviral agents.

The present invention addresses the need for new antiviral drugs that are both disease-modifying and effective in treating patients that are infected with viral hemorrhagic fever (VHFs) viruses. The present invention also addresses the long felt need for new treatments for and means of preventing diseases that involve viral infection and other diseases that involve glucosidase activity.

BRIEF SUMMARY OF THE INVENTION

The present invention is directed toward novel alkylated imino sugars, compounds of formula (I), Including hydrates, solvates, pharmaceutically acceptable salts, prodrugs and complexes thereof, wherein:
A is selected from a group consisting of $(C_2)_3$, $O(CH_2)_2$, $R^1$ at each occurrence is independently selected from the group consisting of hydrogen and $COR^4$;

$R^2$ is selected from a group consisting of hydrogen, optionally substituted $C_{1-6}$ alkyl, optionally substituted cyclic $C_{3-8}$ alkyl, optionally substituted $C_5$-$C_{10}$ bicycloalkyl, $COR^5$, $CO_2R^6$, $SO_2R^7$, $CONHR^8$, and $P(O)(OR^9)_2$;

$R^3$ is selected from a group consisting of hydrogen, optionally substituted $C_{1-6}$ alkyl, optionally substituted cyclic $C_{3-8}$ alkyl, 1-adamantyl, 2-adamantyl, optionally substituted $C_5$-$C_{10}$ bicycloalkyl, and optionally substituted aryl which may be substituted by 0-5 moieties;

$R^3$ and $R^6$ are taken together with the atom to which they are bound to form an optionally substituted ring having 5 ring atoms;

$R^3$ and $R^6$ are taken together with the atom to which they are bound to form

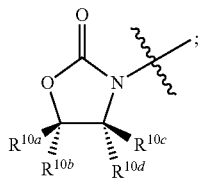

$R^3$ and $R^6$ are taken together with the atom to which they are bound to form

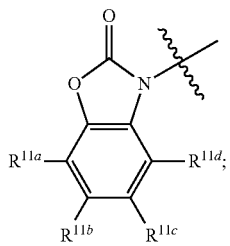

$R^4$ at each occurrence is independently selected from the group consisting of optionally substituted $C_{1-6}$ alkyl and optionally substituted branched $C_{1-6}$ alkyl;

$R^5$ is selected from a group consisting of an optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

$R^6$ is selected from a group consisting of an optionally substituted $C_{1-6}$ alkyl, optionally substituted cyclic $C_{3-8}$ alkyl, optionally substituted $C_5$-$C_{10}$ bicycloalkyl, and optionally substituted branched $C_{1-6}$ alkyl;

$R^7$ is selected from a group consisting of optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

$R^8$ is selected from a group consisting of hydrogen, optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

$R^9$ is selected from a group consisting of optionally substituted $C_{1-6}$ alkyl, optionally substituted $C_5$-$C_{10}$ bicycloalkyl, and optionally substituted cyclic $C_{3-8}$ alkyl;

$R^{10a}$, $R^{10b}$, $R^{10c}$, and $R^{10d}$ are each independently selected from a group consisting of hydrogen, optionally substituted $C_{1-6}$ alkyl, and optionally substituted aryl which may be substituted by 0-5 moieties;

$R^{11a}$, $R^{11b}$, $R^{11c}$, and $R^{11d}$ are each independently selected from a group consisting of hydrogen, halogen, optionally substituted $C_{1-6}$ alkyl, optionally substituted branched $C_{1-6}$ alkyl, and optionally substituted $C_{1-6}$ alkoxy;

The present invention further relates to compositions comprising: an effective amount of one or more compounds according to the present invention and an excipient.

The present invention also relates to a method for treating or preventing diseases that involve infection with viral hemorrhagic fever (VHFs) viruses, including, for example, infection with arenaviruses, filoviruses, bunyaviruses, and flaviviruses, said method comprising administering to a subject an effective amount of a compound or composition according to the present invention.

The present invention yet further relates to a method for treating or preventing diseases that involve infection with viral hemorrhagic fever (VHFs) viruses, including, for example, infection with arenaviruses, filoviruses, bunyaviruses, and flaviviruses, wherein said method comprises administering to a subject a composition comprising an effective amount of one or more compounds according to the present invention and an excipient.

The present invention also relates to a method for treating or preventing disease or conditions associated with infection with arenaviruses, filoviruses, bunyaviruses, and flaviviruses, and diseases that involve infection with viral hemorrhagic fever (VHFs) viruses. Said methods comprise administering to a subject an effective amount of a compound or composition according to the present invention.

The present invention yet further relates to a method for treating or preventing disease or conditions associated with infection with arenaviruses, filoviruses, bunyaviruses, and flaviviruses, and diseases that involve infection with viral hemorrhagic fever (VHFs) viruses, wherein said method comprises administering to a subject a composition comprising an effective amount of one or more compounds according to the present invention and an excipient.

The present invention also relates to a method for treating or preventing disease or conditions associated with infection with viral hemorrhagic fever (VHFs) viruses. Said methods comprise administering to a subject an effective amount of a compound or composition according to the present invention.

The present invention yet further relates to a method for treating or preventing disease or conditions associated with infection with viral hemorrhagic fever (VHFs) viruses, wherein said method comprises administering to a subject a composition comprising an effective amount of one or more compounds according to the present invention and an excipient.

The present invention further relates to a process for preparing the glucosidase inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The glucosidase inhibitors of the present invention are capable of treating and preventing diseases associated with infection with viral hemorrhagic fever (VHFs) viruses, for example infection with arenaviruses, filoviruses, bunyaviruses, and flaviviruses. It has been discovered that viral hemorrhagic fevers (VHF) viruses are enveloped with glycosylated viral proteins and share a similar morphogenesis strategy of budding, making them sensitive to glucosidase inhibitors. This is presumably because the folding of N-linked glycoproteins in these viruses depends upon calnexin, a chaperon that folds proteins that have been trimmed by the ER glucosidase. Most cell functions can compensate for a reduction in glucosidase enzyme function; however, the calnexin dependent viral envelope proteins cannot use alternative processing pathways. Thus, glucosidase inhibitors would be useful as selective antiviral agents against multiple enveloped viruses such as viral hemorrhagic fever (VHFs) viruses, for example arenaviruses, filoviruses, bunyaviruses, and flaviviruses. Without wishing to be limited by theory, it is believed that glucosidase inhibitors of the present invention can ameliorate, abate, otherwise cause to be controlled, diseases associated with infection with viral hemorrhagic fever (VHFs) viruses. Further, without wishing to be limited by theory, it is believed that the novel alkylated imino sugars of the present invention are useful as antiviral agents.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or Spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkylaryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

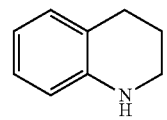

is, for the purposes of the present invention, considered a heterocyclic unit. 6,7-Dihydro-5H-cyclopentapyrimidine having the formula:

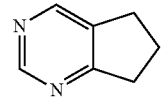

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

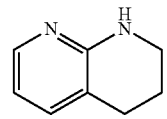

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{12}$, —SR$^{12}$, —N(R$^{12}$)$_2$, —NR$^{12}$C(O)R$^{12}$, —SO$_2$R$^{12}$, —SO$_2$OR$^{12}$, —SO$_2$N(R$^{12}$)$_2$, —C(O)R$^{12}$, —C(O)OR$^{12}$, —C(O)N(R$^{12}$)$_2$, C$_{1-6}$ alkyl, C$_{1-6}$ haloalkyl, C$_{1-6}$ alkoxy, C$_{2-8}$ alkenyl, C$_{2-8}$ alkynyl, C$_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{12}$; wherein R$^{12}$, at each occurrence, independently is hydrogen, —OR$^{13}$, —SR$^{13}$, —C(O)R$^{13}$, —C(O)OR$^1$, —C(O)N(R$^{13}$)$_2$, —SO$_2$R$^{13}$, —S(O)$_2$OR$^{13}$, —N(R$^{13}$)$_2$, —NR$^{13}$C(O)R$^{13}$, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{12}$ units taken together with the atom(s) to which they are bound form an optionally substituted carbocycle or heterocycle wherein said carbocycle or heterocycle has 3 to 7 ring atoms; wherein R$^{13}$, at each occurrence, independently is hydrogen, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{13}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{14}$; for example, —OH, —OCH$_3$, —OCH$_2$CH$_3$, —OCH$_2$CH$_2$CH$_3$;
ii) —C(O)R$^{14}$; for example, —COCH$_3$, —COCH$_2$CH$_3$, —COCH$_2$CH$_2$CH$_3$;
iii) —C(O)OR$^{14}$; for example, —CO$_2$CH$_3$, —CO$_2$CH$_2$CH$_3$, —CO$_2$CH$_2$CH$_2$CH$_3$;
iv) —C(O)N(R$^{14}$)$_2$; for example, —CONH$_2$, —CONHCH$_3$, —CON(CH$_3$)$_2$;
v) —N(R$^{14}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_m$X$_n$; wherein X is halogen, m is from 0 to 2, m+n=3; for example, —CH$_2$F, —CHF$_2$, —CF$_3$, —CCl$_3$, or —CB$_3$;
viii) —SO$_2$R$^{14}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{14}$)C(O)R$^{14}$;
xiii) Oxo (=O);
xiv) Heterocycle; and
xv) Heteroaryl.

wherein each R$^{14}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{14}$ units can be taken together to form a ring comprising 3-7 ring atoms. In certain aspects, each R$^{14}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl.

For the purposes of the present invention the terms "compound," "analog," and "composition of matter" stand equally well for the glucosidase inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{13})_2$, each $R^{13}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Glucosidase Inhibitors

The glucosidase inhibitors of the present invention are alkylated imino sugars, and include all enantiomeric and diastereomeric forms and pharmaceutically accepted salts thereof having the formula (I):

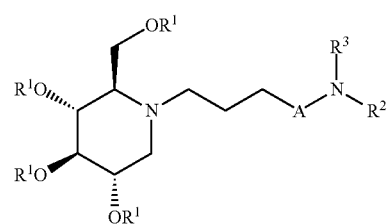

Including hydrates, solvates, pharmaceutically acceptable salts, prodrugs and complexes thereof, wherein:

A is selected from a group consisting of $(C_2)_3$, $O(CH_2)_2$,

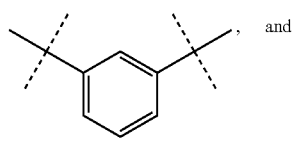 , and

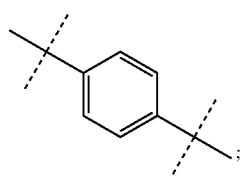 ;

$R^1$ at each occurrence is independently selected from the group consisting of hydrogen and $COR^4$;

$R^2$ is selected from a group consisting of hydrogen, optionally substituted $C_{1-6}$ alkyl, optionally substituted cyclic $C_{3-8}$ alkyl, optionally substituted $C_5$-$C_{10}$ bicycloalkyl, $COR^5$, $CO_2R^6$, $SO_2R^7$, $CONHR^8$, and $P(O)(OR^9)_2$;

$R^3$ is selected from a group consisting of hydrogen, optionally substituted $C_{1-6}$ alkyl, optionally substituted cyclic $C_{3-8}$ alkyl, 1-adamantyl, 2-adamantyl, optionally substituted $C_5$-$C_{10}$ bicycloalkyl, and optionally substituted aryl which may be substituted by 0-5 moieties;

$R^3$ and $R^6$ are taken together with the atom to which they are bound to form an optionally substituted ring having 5 ring atoms;

$R^3$ and $R^6$ are taken together with the atom to which they are bound to form

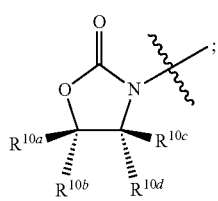

$R^3$ and $R^6$ are taken together with the atom to which they are bound to form

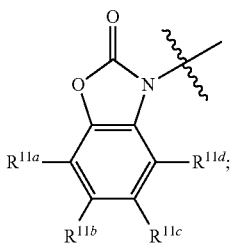

R⁴ at each occurrence is independently selected from the group consisting of optionally substituted $C_{1-6}$ alkyl and optionally substituted branched $C_{1-6}$ alkyl;

R⁵ is selected from a group consisting of an optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

R⁶ is selected from a group consisting of an optionally substituted $C_{1-6}$ alkyl, optionally substituted cyclic $C_{3-8}$ alkyl, optionally substituted $C_5$-$C_{10}$ bicycloalkyl, and optionally substituted branched $C_{1-6}$ alkyl;

R⁷ is selected from a group consisting of optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

R⁸ is selected from a group consisting of hydrogen, optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

R⁹ is selected from a group consisting of optionally substituted $C_{1-6}$ alkyl, optionally substituted $C_5$-$C_{10}$ bicycloalkyl, and optionally substituted cyclic $C_{3-8}$ alkyl;

$R^{10a}$, $R^{10b}$, $R^{10c}$, and $R^{10d}$ are each independently selected from a group consisting of hydrogen, optionally substituted $C_{1-6}$ alkyl, and optionally substituted aryl which may be substituted by 0-5 moieties;

$R^{11a}$, $R^{11b}$, $R^{11c}$, and $R^{11d}$ are each independently selected from a group consisting of hydrogen, halogen, optionally substituted $C_{1-6}$ alkyl, optionally substituted branched $C_{1-6}$ alkyl, and optionally substituted $C_{1-6}$ alkoxy;

In some embodiments A is $(CH_2)_3$.
In some embodiments A is $O(CH_2)_2$.
In some embodiments A is

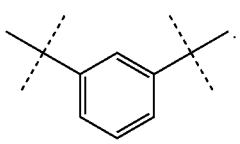

In some embodiments A is

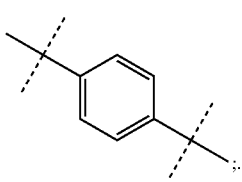

In some embodiments R¹ is hydrogen.
In some embodiments R¹ is COR⁴.
In some embodiments R¹ is $COCH_3$, $COCH(CH_3)_2$, or $CO(CH_2)_2CH_3$.
In some embodiments R² is hydrogen.
In some embodiments R² is optionally substituted $C_{1-6}$ alkyl.
In some embodiments R² is optionally substituted cyclic $C_{3-8}$ alkyl.
In some embodiments R² is optionally substituted $C_5$-$C_{10}$ bicycloalkyl.
In some embodiments R² is COR⁵.
In some embodiments R² is $CO_2R^6$.
In some embodiments R² is $SO_2R^7$.
In some embodiments R² is CONHR⁸.
In some embodiments R² is and $P(O)(OR^9)_2$.
In some embodiments R² is Cyclohexyl, $COCH_3$, $CO_2C(CH_3)_3$, $COCH(CH_3)_2$, $COCH_2C(CH_3)_3$, $COC(CH_3)_3$, $SO_2CH_3$, $SO_2C(CH_3)_3$, $SO_2Phenyl$, $CONHC(CH_3)_3$, COPhenyl, $PO(OCH_2CH_3)_2$, CONHPhenyl, $CONHCH_2CH_3$, or $CONH_2$.
In some embodiments R³ is hydrogen.
In some embodiments R³ is optionally substituted $C_{1-6}$ alkyl.
In some embodiments R³ is optionally substituted cyclic $C_{3-8}$ alkyl.
In some embodiments R³ is optionally substituted aryl which may be substituted by 0-5 moieties.
In some embodiments R³ is optionally substituted $C_5$-$C_{10}$ bicycloalkyl.
In some embodiments R³ is Cyclopropyl, Cyclobutyl, Cyclopentyl, Cyclohexyl, Cycloheptyl, 2-methylcyclohexyl, 1-Adamantyl, 2-Adamantyl, 2,5-difluorophenyl, or 2,4-difluorophenyl.
In some embodiments R⁴ is optionally substituted $C_{1-6}$ alkyl.
In some embodiments R⁴ is optionally substituted branched $C_{1-6}$ alkyl.
In some embodiments R⁵ is optionally substituted $C_{1-6}$ alkyl.
In some embodiments R⁵ is optionally substituted branched $C_{1-6}$ alkyl.
In some embodiments R⁵ is optionally substituted cyclic $C_{3-8}$ alkyl.
In some embodiments R⁵ is optionally substituted $C_5$-$C_{10}$ bicycloalkyl.
In some embodiments R⁵ is optionally substituted aryl which may be substituted by 0-5 moieties.
In some embodiments R⁵ is methyl, isopropyl, tert-butyl, 2-methylpropyl, phenyl, 2,4-difluorophenyl, 2,5-difluorophenyl, or 2,4,5-trifluorophenyl.
In some embodiments R⁶ is optionally substituted $C_{1-6}$ alkyl.
In some embodiments R⁶ is optionally substituted branched $C_{1-6}$ alkyl.
In some embodiments R⁶ is optionally substituted cyclic $C_{3-8}$ alkyl.
In some embodiments R⁶ is optionally substituted $C_5$-$C_{10}$ bicycloalkyl.
In some embodiments R⁶ is tert-butyl.
In some embodiments R⁷ is optionally substituted $C_{1-6}$ alkyl.
In some embodiments R⁷ is optionally substituted branched $C_{1-6}$ alkyl.
In some embodiments R⁷ is optionally substituted aryl which may be substituted by 0-5 moieties.

In some embodiments $R^7$ is optionally substituted cyclic $C_{3-8}$ alkyl.

In some embodiments $R^7$ is optionally substituted $C_5$-$C_{10}$ bicycloalkyl.

In some embodiments $R^7$ is methyl, tert-butyl, or phenyl.

In some embodiments $R^8$ is hydrogen.

In some embodiments $R^8$ is optionally substituted $C_{1-6}$ alkyl.

In some embodiments $R^8$ is optionally substituted branched $C_{1-6}$ alkyl.

In some embodiments $R^8$ is optionally substituted cyclic $C_{3-8}$ alkyl.

In some embodiments $R^8$ is optionally substituted $C_5$-$C_{10}$ bicycloalkyl.

In some embodiments $R^8$ is optionally substituted aryl which may be substituted by 0-5 moieties.

In some embodiments $R^8$ is ethyl, tert-butyl, or phenyl.

In some embodiments $R^9$ is optionally substituted $C_{1-6}$ alkyl.

In some embodiments $R^9$ is optionally substituted cyclic $C_{3-8}$ alkyl.

In some embodiments $R^9$ is optionally substituted $C_5$-$C_{10}$ bicycloalkyl.

In some embodiments $R^9$ is ethyl.

In some embodiments $R^3$ and $R^6$ are taken together with the atom to which they are bound to form an optionally substituted ring having 5 ring atoms.

In some embodiments $R^3$ and $R^6$ are taken together with the atom to which they are bound to form

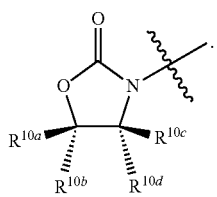

In some embodiments $R^{10a}$ is hydrogen.

In some embodiments $R^{10a}$ is optionally substituted $C_{1-6}$ alkyl.

In some embodiments $R^{10a}$ is optionally substituted aryl which may be substituted by 0-5 moieties.

In some embodiments $R^{10a}$ is phenyl.

In some embodiments $R^{10b}$ is hydrogen.

In some embodiments $R^{10b}$ is optionally substituted $C_{1-6}$ alkyl.

In some embodiments $R^{10b}$ is optionally substituted aryl which may be substituted by 0-5 moieties.

In some embodiments $R^{10b}$ is phenyl.

In some embodiments $R^{10c}$ is hydrogen.

In some embodiments $R^{10c}$ is optionally substituted $C_{1-6}$ alkyl.

In some embodiments $R^{10c}$ is optionally substituted aryl which may be substituted by 0-5 moieties.

In some embodiments $R^{10d}$ is hydrogen.

In some embodiments $R^{10d}$ is optionally substituted $C_{1-6}$ alkyl.

In some embodiments $R^{10d}$ is optionally substituted aryl which may be substituted by 0-5 moieties.

In some embodiments $R^3$ and $R^6$ are taken together with the atom to which they are bound to form

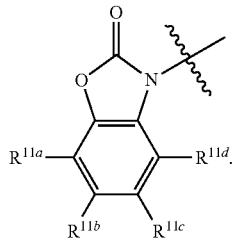

In some embodiments $R^{11a}$ is hydrogen.

In some embodiments $R^{11a}$ is halogen.

In some embodiments $R^{11a}$ is optionally substituted $C_{1-6}$ alkyl.

In some embodiments $R^{11a}$ is optionally substituted branched $C_{1-6}$ alkyl In some embodiments $R^{11a}$ is optionally substituted $C_{1-6}$ alkoxy.

In some embodiments $R^{11b}$ is hydrogen.

In some embodiments $R^{11b}$ is halogen.

In some embodiments $R^{11b}$ is optionally substituted $C_{1-6}$ alkyl.

In some embodiments $R^{11b}$ is optionally substituted branched $C_{1-6}$ alkyl In some embodiments $R^{11b}$ is optionally substituted $C_{1-6}$ alkoxy.

In some embodiments $R^{11b}$ is hydrogen.

In some embodiments $R^{11b}$ is halogen.

In some embodiments $R^{11b}$ is optionally substituted $C_{1-6}$ alkyl.

In some embodiments $R^{11b}$ is optionally substituted branched $C_{1-6}$ alkyl In some embodiments $R^{11b}$ is optionally substituted $C_{1-6}$ alkoxy.

In some embodiments $R^{11c}$ is hydrogen.

In some embodiments $R^{11c}$ is halogen.

In some embodiments $R^{11c}$ is optionally substituted $C_{1-6}$ alkyl.

In some embodiments $R^{11c}$ is optionally substituted branched $C_{1-6}$ alkyl In some embodiments $R^{11c}$ is optionally substituted $C_{1-6}$ alkoxy.

In some embodiments $R^{11d}$ is hydrogen.

In some embodiments $R^{11d}$ is halogen.

In some embodiments $R^{11d}$ is optionally substituted $C_{1-6}$ alkyl.

In some embodiments $R^{11d}$ is optionally substituted branched $C_{1-6}$ alkyl In some embodiments $R^{11d}$ is optionally substituted $C_{1-6}$ alkoxy.

Exemplary embodiments include compounds having the formula (II) or a pharmaceutically acceptable salt form thereof:

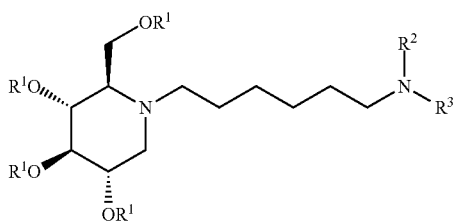

(II)

wherein non-limiting examples of $R^1$, $R^2$, and $R^3$ are defined herein below in Table 1.

TABLE 1

| Entry | $R^1$ | $R^2$ | $R^3$ |
|---|---|---|---|
| 1 | H | $CO_2C(CH_3)_3$ | 2-methylCyclohexyl |
| 2 | H | H | 2-methylcyclohexyl |
| 3 | H | $COC(CH_3)_3$ | 2-methylcyclohexyl |
| 4 | H | $COCH_3$ | Cyclohexyl |
| 5 | H | Cyclohexyl | Cyclohexyl |
| 6 | H | $CO_2C(CH_3)_3$ | H |
| 7 | H | $COC(CH_3)_3$ | Cyclohexyl |
| 8 | H | $COCH_3$ | 2,5-difluorophenyl |
| 9 | H | $COCH_3$ | 2,4-difluorophenyl |
| 10 | H | $COC(CH_3)_3$ | 2,5-difluorophenyl |
| 11 | H | $COC(CH_3)_3$ | 2,4-difluorophenyl |
| 12 | H | $COCH(CH_3)_2$ | Cyclohexyl |
| 13 | H | $COCH_2C(CH_3)_3$ | Cyclohexyl |
| 14 | H | $COC(CH_3)_3$ | Cyclopropyl |
| 15 | H | $COC(CH_3)_3$ | Cyclobutyl |
| 16 | H | $COC(CH_3)_3$ | Cyclopentyl |
| 17 | H | $COC(CH_3)_3$ | Cycloheptyl |
| 18 | H | $COC(CH_3)_3$ | 2-Adamantyl |
| 19 | H | $COC(CH_3)_3$ | 1-Adamantyl |
| 20 | H | $SO_2CH_3$ | Cyclohexyl |
| 21 | H | $SO_2C(CH_3)_3$ | Cyclohexyl |
| 22 | H | SO2Phenyl | Cyclohexyl |
| 23 | H | $CONHC(CH_3)_3$ | Cyclohexyl |
| 24 | H | COPhenyl | Cyclohexyl |
| 25 | H | $PO(OCH_2CH_3)_2$ | Cyclohexyl |
| 26 | H | CONHPhenyl | Cyclohexyl |
| 27 | H | $CONHCH_2CH_3$ | Cyclohexyl |
| 28 | H | $CONH_2$ | Cyclohexyl |
| 29 | $CO(CH_2)_2CH_3$ | $COC(CH_3)_3$ | Cyclohexyl |
| 30 | $CO(CH_2)_2CH_3$ | $SO_2CH_3$ | Cyclohexyl |
| 31 | $COCH(CH_3)_2$ | $SO_2CH_3$ | Cyclohexyl |
| 32 | $COCH(CH_3)_2$ | $COC(CH_3)_3$ | Cyclohexyl |
| 33 | $COCH_3$ | $COC(CH_3)_3$ | Cyclohexyl |
| 34 | $COCH_3$ | $SO_2CH_3$ | Cyclohexyl |

Exemplary embodiments include compounds having the formula (III) or a pharmaceutically acceptable salt form thereof:

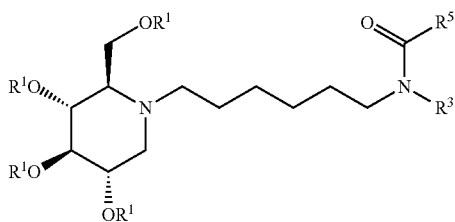

(III)

wherein non-limiting examples of $R^1$, $R^3$, and $R^5$ are defined herein below in Table 2.

TABLE 2

| Entry | $R^1$ | $R^3$ | $R^5$ |
|---|---|---|---|
| 1 | H | Cyclohexyl | 2,4-difluorophenyl |
| 2 | H | Cyclohexyl | 2,5-difluorophenyl |
| 3 | H | Cyclohexyl | 2,4,5-trifluorophenyl |

Exemplary embodiments include compounds having the formula (IV) or a pharmaceutically acceptable salt form thereof:

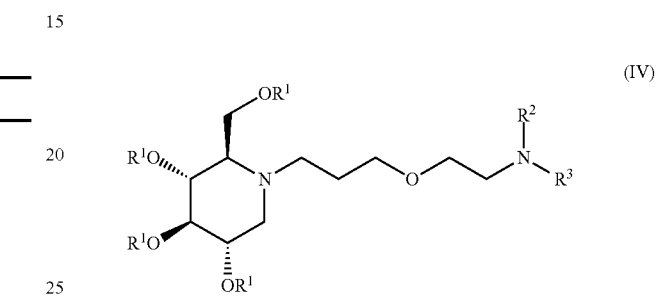

(IV)

wherein non-limiting examples of $R^1$, $R^2$, and $R^3$ are defined herein below in Table 3.

TABLE 3

| Entry | $R^1$ | $R^2$ | $R^3$ |
|---|---|---|---|
| 1 | H | Cyclohexyl | $CONHC(CH_3)_3$ |
| 2 | H | Cyclohexyl | COPhenyl |
| 3 | H | Cyclohexyl | $COC(CH_3)_3$ |

Exemplary embodiments include compounds having the formula (V) or a pharmaceutically acceptable salt form thereof:

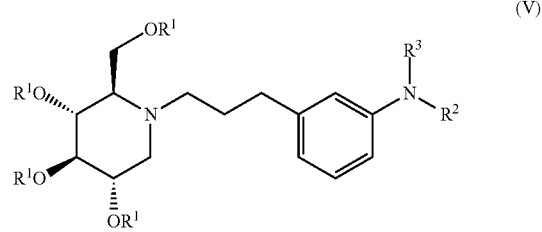

(V)

wherein non-limiting examples of $R^1$, $R^2$, and $R^3$ are defined herein below in Table 4.

TABLE 4

| Entry | $R^1$ | $R^2$ | $R^3$ |
|---|---|---|---|
| 1 | H | $COC(CH_3)_3$ | H |

Exemplary embodiments include compounds having the formula (VI) or a pharmaceutically acceptable salt form thereof:

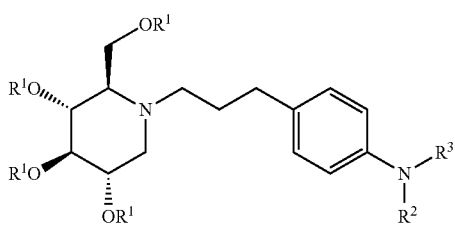

(VI)

wherein non-limiting examples of $R^1$, $R^2$, and $R^3$ are defined herein below in Table 5.

TABLE 5

| Entry | $R^1$ | $R^2$ | $R^3$ |
|---|---|---|---|
| 1 | H | $COC(CH_3)_3$ | H |

Exemplary embodiments include compounds having the formula (VII) or a pharmaceutically acceptable salt form thereof:

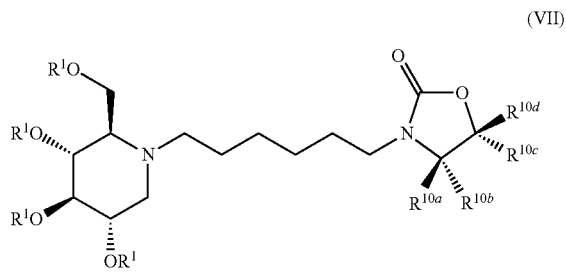

(VII)

wherein non-limiting examples of $R^{10a}$, $R^{10b}$, $R^{10c}$ and $R^{10d}$ are defined herein below in Table 6.

TABLE 6

| Entry | $R^1$ | $R^{10a}$ | $R^{10b}$ | $R^{10c}$ | $R^{10d}$ |
|---|---|---|---|---|---|
| 1 | H | Phenyl | H | H | H |
| 2 | H | H | Phenyl | H | H |

Exemplary embodiments include compounds having the formula (VIII) or a pharmaceutically acceptable salt form thereof:

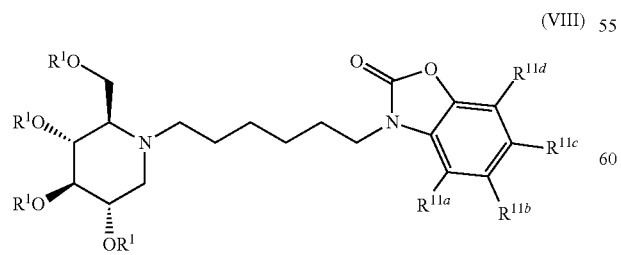

(VIII)

wherein non-limiting examples of $R^{11a}$, $R^{11b}$, $R^{11c}$, and $R^{11d}$ are defined herein below in Table 7.

TABLE 7

| Entry | $R^1$ | $R^{11a}$ | $R^{11b}$ | $R^{11c}$ | $R^{11d}$ |
|---|---|---|---|---|---|
| 1 | H | H | H | H | H |

For the purposes of demonstrating the manner in which the compounds of the present invention are named and referred to herein, the compound having the formula:

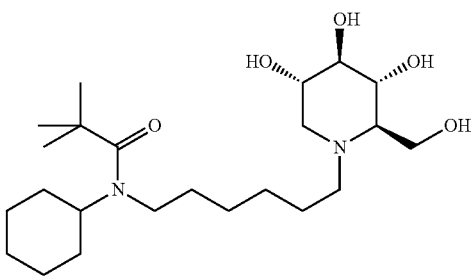 [SMILES: CC(C)(C)C(=O)N(CCCCCCN1C[C@H](O)[C@@H](O)[C@H](O)[C@H]1CO)C1CCCCC1]

has the chemical name (R,R,S,R)—N-Cyclohexyl-2,2-dimethyl-N-[6-(3,4,5-trihydroxy-2-hydroxymethyl-piperidin-1-yl)-hexyl]-propionamide.

For the purposes of the present invention, a compound depicted by the diastereomeric formula, for example:

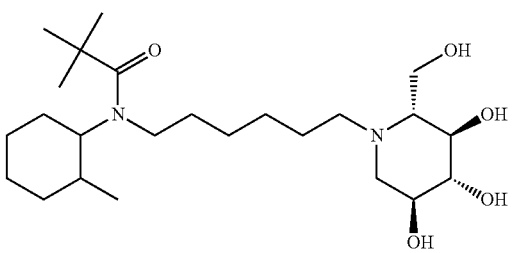 [SMILES: CC1CCCCC1N(CCCCCCN1C[C@H](O)[C@@H](O)[C@H](O)[C@H]1CO)C(=O)C(C)(C)C]

will stand equally well for either of the four diasteromers having the formula:

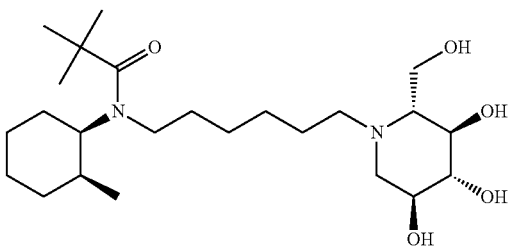 [SMILES: C[C@H]1CCCC[C@H]1N(CCCCCCN1C[C@H](O)[C@@H](O)[C@H](O)[C@H]1CO)C(=O)C(C)(C)C]

or the formula:

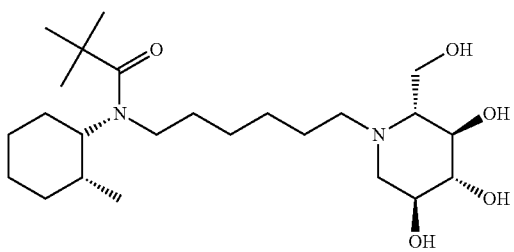

or the formula:

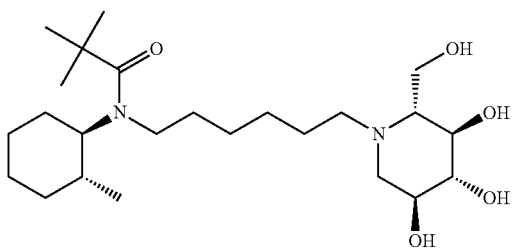 [SMILES: C[C@@H]1CCCC[C@H]1N(CCCCCCN1C[C@H](O)[C@@H](O)[C@H](O)[C@H]1CO)C(=O)C(C)(C)C]

or the formula:

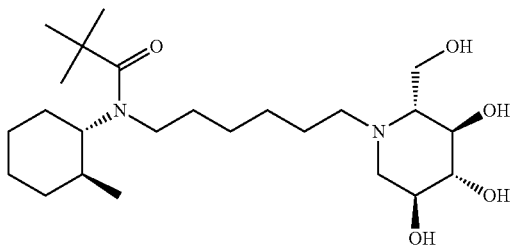 [SMILES: C[C@H]1CCCC[C@@H]1N(CCCCCCN1C[C@H](O)[C@@H](O)[C@H](O)[C@H]1CO)C(=O)C(C)(C)C]

or mixtures thereof.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the novel alkylated imino sugars of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

General Synthetic Schemes for Preparation of Compounds.

The reagents used in the preparation of the compounds of this invention can be either commercially obtained or can be prepared by standard procedures described in the literature. In accordance with this invention, compounds in the genus may be produced by one of the following reaction schemes.

The first aspect of the process of the present invention relates to a process for preparing novel alkylated imino sugars having the formula (I). Compounds of formula (I) may be prepared according to the process outlined in Scheme 1.

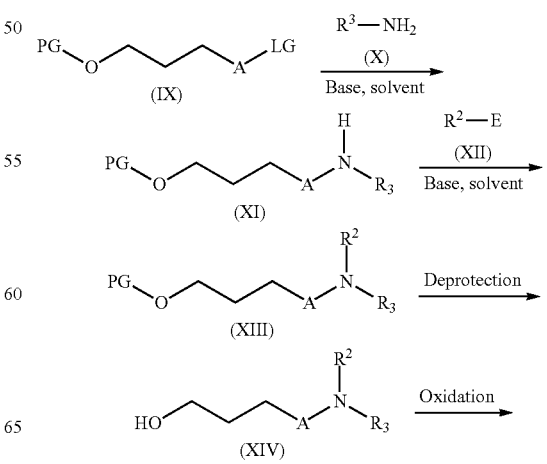

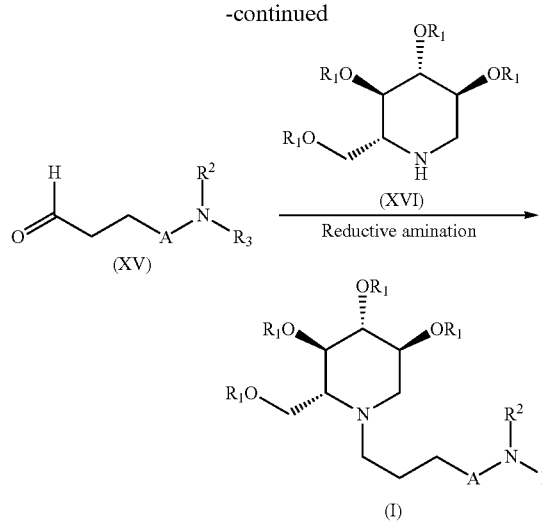

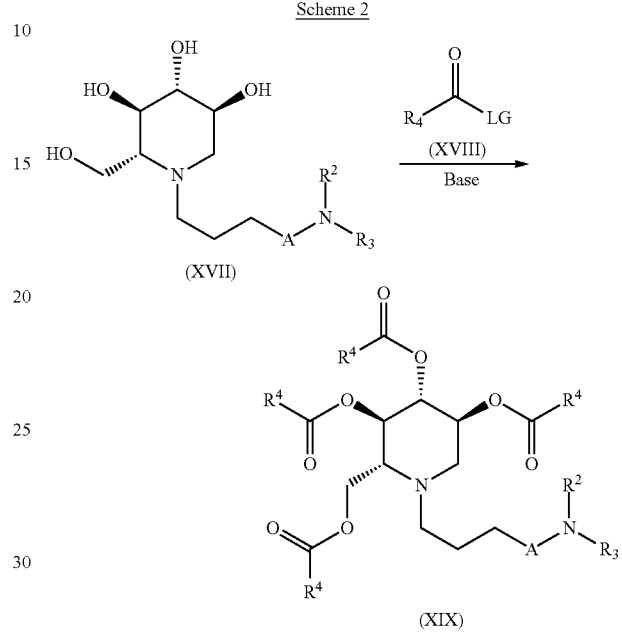

Accordingly, a suitably substituted compound of the formula (IX), a known compound or compound prepared by known methods, is reacted with a suitably substituted compound of the formula (X) in the presence of a base such as potassium carbonate, sodium carbonate, cesium carbonate, triethyl amine, pyridine, sodium hydride, Lithium bis(trimethylsilyl)amide, lithium diisopropyl amide, and the like, in an organic solvent such as acetonitrile, tetrahydronfuran, 1,4-dioxane, dimethylformamide, methylene chloride, dichloroethane, and the like to give a compound of the formula (XI). A compound of the formula (XI) is then reacted with an electrophile (XII) containing $R^2$ such as an acyl halide, sulfonyl halide, phosphoryl halide, and isocyanate to give a compound of the formula (XIII). The protecting group in a compound of the formula (XIII) can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as litium hydroxide, sodium hydroxide, potassium carbonate and the like in a solvent like water, methanol, tetrahydrofuran and the like or 4) with tetrabutyl ammonium fluoride in an organic solvent such as tetrahydrofuran, 1,4-dioxane, methylene chloride, methanol and the like, to provide a compound of the formula (XIV). A compound of the formula (XIV) is then treated with Dess Martin reagent (1,1,1-Triacetoxy-1,1-dihydro-1,2-benziodoxol-3(1H)-one) in an organic solvent such as methylene chloride, dichloroethane, tetrahydrofuran, 1,4-dioxane, and the like to provide a compound of the formula (XV). Alternatively, a compound of the formula (XIV) may be treated with pyridinium chlorochromate (PCC) in an organic solvent such as methylene chloride, dichloroethane, tetrahydrofuran, 1,4-dioxane, and the like to provide a compound of the formula (XV). Alternatively, a compound of the formula (XIV) may be treated with a preformed mixture of oxalyl chloride and dimethyl sulfoxide in an organic solvent such as methylene chloride, dichloroethane, tetrahydrofuran, 1,4-dioxane, and the like, followed by a base such as triethyl amine, diisopropyl amine and the like to provide a compound of the formula (XV). A compound of the formula (XV) is then treated with a compound of the formula (XVI) in the presence of hydrogen and in the presence of a suitable catalyst such as 5% palladium on carbon, 10% palladium on carbon and the like, in an organic solvent such as methanol, ethanol, tetrahydrofuran, 1,4-dioxane and the like to provide a compound of the formula (I).

In another aspect of the invention, compounds of the formula (XIX) may be prepared according to according to the process outlined in Scheme 2.

Accordingly, a suitably substituted compound of the formula (XVII) is reacted with a suitably substituted compound of the formula (XVIII) in the presence of a base such as pyridine, triethyl amine, diisopropylethyl amine, and the like, optionally in an organic solvent such as methylene chloride, dichloroethane, acetonitrile, tetrahydronfuran, 1,4-dioxane, dimethylformamide and the like to give a compound of the formula (XIX).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

Exemplary Procedures:

The following exemplary procedures provide methods for preparing representative compounds of formula (I). The skilled practitioner will know how to substitute the appropriate reagents, starting materials and purification methods known to those skilled in the art, in order to prepare additional compounds of the present invention.

$^1$H NMR spectra were recorded on a 300 MHz INOVA VARIAN spectrometer. Chemical shifts values are given in ppm and referred as the internal standard to TMS (tetramethylsilane). The peak patterns are indicated as follows: s, singlet; d, doublet; t, triplet; q, quadruplet; m, multiplet and dd, doublet of doublets. The coupling constants (J) are reported in Hertz (Hz). Mass Spectra were obtained on a 1200 Aligent LC-MS spectrometer (ES-API, Positive). Silica gel column chromatography was performed over silica gel 100-200 mesh, and the eluent was a mixture of ethyl acetate and hexanes, or mixture of methanol and ethyl acetate. All the tested compounds possess a purity of at least 95%. Analytical HPLC was run on the Agilent 1100 HPLC instrument, equipped with Agilent, ZORBAX SB-C18 column and UV detection at 210 nm.

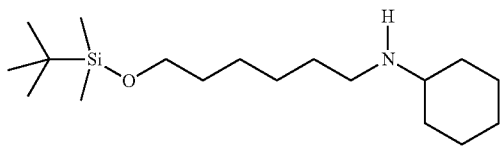 [SMILES: CC(C)(C)[Si](C)(C)OCCCCCCNC1CCCCC1]

N-(6-((tert-butyldimethylsilyl)oxy)hexyl)cyclohexanamine: In a sealed tube was charged with ((6-bromohexyl)oxy)(tert-butyl)dimethylsilane (2.35 mL, 8.45 mmol), cyclohexanamine (1.95 mL, 16.9 mmol), potassium carbonate (2.34 g, 16.9 mmol), and acetonirile (6 mL). The mixture was stirred at 80° C. for 2.5 days and filtered through a pad of celite. The solution was concentrated and purified on silica gel with a eluent of Methanol (2N NH$_3$):methylene chloride from 0:1 to 5:95 to give a clear oil (2.4 g, 90%). $^1$H NMR (300 MHz, CDCl$_3$): δ 3.55 (t, J=6.4 Hz, 2H), 2.56 (t, J=7.0 Hz, 2H), 2.42-2.28 (m, 1H), 1.89-1.78 (m, 2H), 1.74-1.62 (m, 2H), 1.62-1.52 (m, 2H), 1.52-1.36 (m, 4H), 1.36-1.22 (m, 5H), 1.22-0.92 (m, 5H), 0.85 (s, 9H), 0.05 (s, 6H).

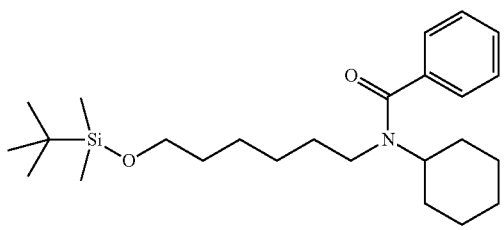 [SMILES: CC(C)(C)[Si](C)(C)OCCCCCCN(C(=O)c1ccccc1)C1CCCCC1]

N-(6-((tert-butyldimethylsilyl)oxy)hexyl)-N-cyclohexylbenzamide: To a solution of N-(6-((tert-butyldimethylsilyl)oxy)hexyl)cyclohexanamine (208 mg, 0.66 mmol) and triethyl amine (0.19 mL, 1.32 mmol) in methylene chloride (5 mL) at 0° C. was added benzoyl chloride (0.092 mL, 0.80 mmol). The mixture was stirred for 2 hours before it was diluted with ethyl acetate and washed with saturated bicarbonate solution nd brine. The organic phase was separated and concentrated. Purification on silica gel with ethyl acetate: hexanes from 0:1 to 2:8 provided desired product as a clear oil (242.2 mg, 88%). $^1$H NMR (300 MHz, CDCl$_3$): δ 7.40-7.20 (m, 5H), 3.64-2.95 (m, 5H), 1.95-0.88 (m, 18H), 0.83 (s, 9H), 0.00 (s, 6H).

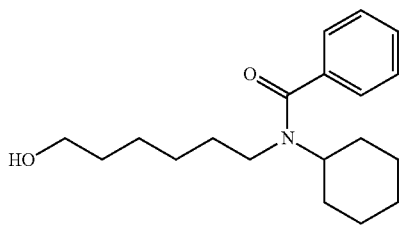 [SMILES: O=C(c1ccccc1)N(CCCCCCO)C1CCCCC1]

N-cyclohexyl-N-(6-hydroxyhexyl)benzamide: N-(6-((tert-butyldimethylsilyl)oxy) hexyl)-N-cyclohexylbenzamide (242 mg, 0.58 mmol) was dissolved in THF (2 mL) and treated with TBAF (1M in THF, 0.72 mL, 0.72 mmol). The mixture was stirred at room temperature for overnight. The mixture was then concentrated and purified on silica gel with ethyl acetate:hexanes from 2:8 to 1:1 gave the desired product as a clear oil (136 mg, 77%). $^1$H NMR (300 MHz, CDCl$_3$): δ 7.42-7.29 (m, 5H), 3.75-2.98 (m, 5H), 1.98-0.80 (m, 19H).

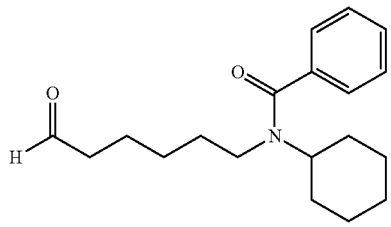 [SMILES: O=CCCCCCN(C(=O)c1ccccc1)C1CCCCC1]

N-cyclohexyl-N-(6-oxohexyl)benzamide: N-cyclohexyl-N-(6-hydroxyhexyl)benzamide (136 mg, 0.45 mmol) was dissolved in methylene chloride (6 mL) and treated with Dess-Martin reagent (247.0 mg, 0.58 mmol). The oxidation was finished in 4 hours. The mixture was diluted with methylene chloride and washed with saturated bicarbonate and sodium thiosulfate (5%). The organic phase was concentrated and purified on silica gel with ethyl acetate: hexanes from 0:1 to 2:8 gave the desired product as a clear oil (108.2 mg, 80%). $^1$H NMR (300 MHz, CDCl$_3$): δ 9.80 (s, 1H), 7.46-7.28 (m, 5H), 3.60-2.98 (m, 3H), 2.60-2.15 (m, 2H), 1.95-0.80 (m, 16H).

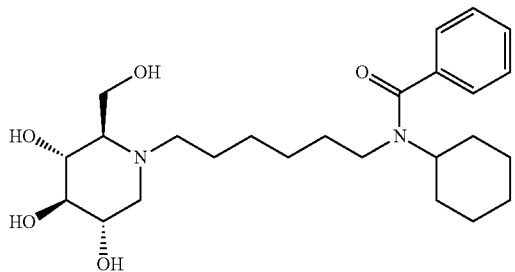 [SMILES: O=C(c1ccccc1)N(CCCCCCN1C[C@H](O)[C@@H](O)[C@H](O)[C@H]1CO)C1CCCCC1]

N-cyclohexyl-N-(6-((2R,3R,4R,5S)-3,4,5-trihydroxy-2-(hydroxymethyl)piperidin-1-yl)hexyl)benzamide: A solution of DNJ (47 mg, 0.29 mmol) in acetic acid (2 mL) was stirred at room temperature for an hour, and then the solvent was removed under reduced pressure. The resulting residue was treated with 200 proof ethanol (5 mL) and the aldehyde prepared above (108.2 mg, 0.36 mmol). Then, it was transferred to the hydrogenation bottle, followed by addition of 10% Pd/C (32 mg) and 200 proof ethanol (5 mL). The mixture was hydrogenated under 45 psi of H$_2$ for 24 hours. After the reaction was complete, it was treated with celite (100 mg), and then filtered through a celite pad. The filtrate was concentrated and purified through silica gel column chromatography (methanol:ethyl acetate=5:95 to 15:85) to afford the product as a white solid (61 mg, 47%). $^1$H NMR (300 MHz, CD$_3$OD): δ 7.50-7.42 (m, 3H), 7.37-7.29 (m, 2H), 3.94-2.75 (m, 2H), 3.58-3.30 (m, 4H), 3.30-3.00 (m, 3H), 3.00-2.78 (m, 1H), 2.78-2.50 (m, 1H), 2.50-2.00 (m, 2H), 2.00-1.20 (m, 15H), 1.20-0.80 (m, 3H). Calculated MS for C$_{25}$H$_{40}$N$_2$O$_5$, 448.29; observed, 449.3.

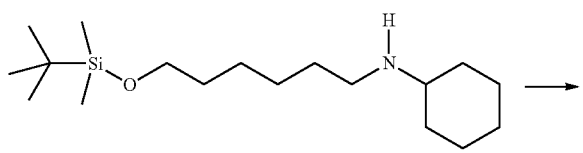

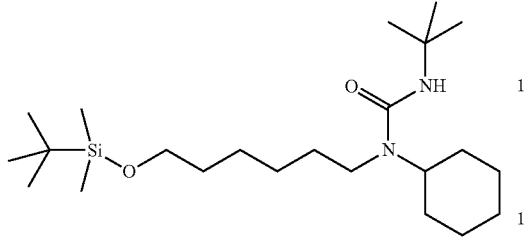

3-(tert-butyl)-1-(6-((tert-butyldimethylsilyl)oxy)hexyl)-1-cyclohexylurea: To a solution of N-(6-((tert-butyldimethylsilyl)oxy)hexyl)cyclohexanamine (330 mg, 1.05 mmol) in tetrahydrofuran (5 mL) at 0° C. was added 2-isocyanato-2-methylpropane (0.14 mL, 1.16 mmol). The mixture was stirred for 2 hours before it was quenched with methanol, and concentrated. Purification on silica gel with ethyl acetate: hexanes from 0:1 to 1:9 provided desired product as a clear oil (494.1 mg, 114%). $^1$H NMR (300 MHz, CDCl$_3$): δ 4.11 (s, 1H), 3.99-3.84 (m, 1H), 3.56 (t, J=6.4 Hz, 2H), 2.92 (t, J=8.2 Hz, 2H), 1.80-0.94 (m, 18H), 0.85 (s, 9H), 0.05 (s, 6H).

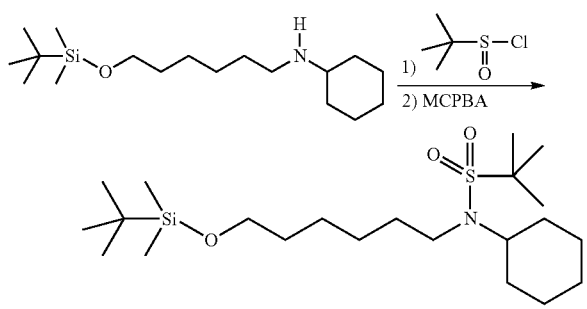

N-(6-((tert-butyldimethylsilyl)oxy)hexyl)-N-cyclohexyl-2-methylpropane-2-sulfonamide: To a solution of N-(6-((tert-butyldimethylsilyl)oxy)hexyl)cyclohexanamine (246 mg, 0.78 mmol) and triethyl amine (0.22 mL, 1.57 mmol) in methylene chloride (10 mL) at 0° C. was added 2-methylpropane-2-sulfinic chloride (0.13 mL, 1.01 mmol). The mixture was stirred for 2 hours before it was diluted with ethyl acetate and washed with saturated bicarbonate solution and brine. The organic phase was separated and concentrated. Purification on silica gel with ethyl acetate: hexanes from 0:1 to 3:7 provided desired compound, N-(6-((tert-butyldimethylsilyl)oxy)hexyl)-N-cyclohexyl-2-methylpropane-2-sulfinamide, as a clear oil (282.5 mg, 87%). $^1$H NMR (300 MHz, CDCl$_3$): δ 3.55 (t, J=6.4 Hz, 2H), 3.14 (ddd, J=5.3, 11.7, 14.3 Hz, 1H), 2.94-2.76 (m, 1H), 2.64-2.46 (m, 1H), 2.04-1.92 (m, 2H), 1.84-1.64 (m, 3H), 1.64-1.38 (m, 7H), 1.38-0.94 (m, 6H), 1.14 (s, 9H), 0.85 (s, 9H), 0.05 (s, 6H).

The N-(6-((tert-butyldimethylsilyl)oxy)hexyl)-N-cyclohexyl-2-methylpropane-2-sulfinamide was dissolved in methylene chloride (5 mL), cooled with an ice bath, and treated with meta-chloroperoxybenzoic acid (205.3 mg, 0.92 mmol, 1.25 eq). The mixture was stirred at room temperature for 3 hours, and diluted with methylene chloride and washed with Na$_2$S$_2$O$_3$ and brine, and then concentrated. The residue was purified on silica gel with a gradient of ethyl acetate: hexanes from 0:1 to 1:9 provided a clear oil (316 mg, 100%). $^1$H NMR (300 MHz, CDCl$_3$): δ 3.61 (t, J=6.4 Hz, 2H), 3.48 (tt, J=2.9, 12.0 Hz, 1H), 3.19 (t, J=7.9 Hz, 2H), 2.00-1.74 (m, 4H), 1.74-1.52 (m, 6H), 1.52-1.20 (m, 3H), 1.38 (s, 9H), 1.20-1.00 (m, 1H), 0.85 (s, 9H), 0.05 (s, 6H).

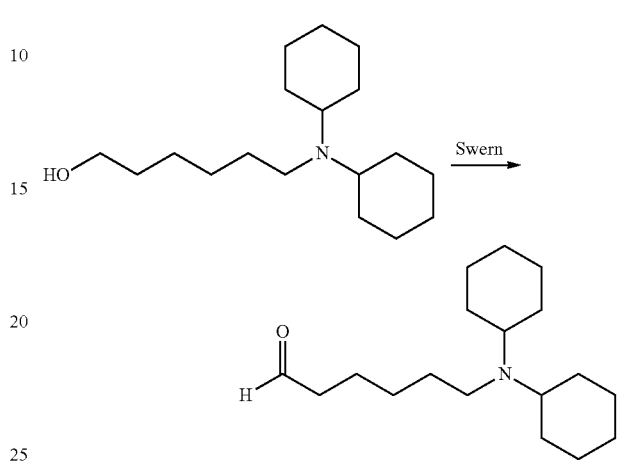

6-(dicyclohexylamino)hexanal: Dimethyl sulfoxide (0.20 mL, 2.88 mmol) in methylene chloride (1 mL) was added dropwise to a stirred solution of oxalyl chloride (0.12 mL, 1.44 mmol) in methylene chloride (3 mL) at −78° C. The mixture was stirred for 15 minutes before 6-(dicyclohexylamino)hexan-1-ol (203 mg, 0.72 mmol) in methylene chloride (3 mL) was added. The mixture was stirred at this temperature for an hour and treated with triethylamine (1.0 mL, 7.2 mmol). The reaction temperature was raised to room temperature over a course of 1.5 hour. Saturated ammonium chloride was added and the mixture was extracted with dichloromethane. The organic phase was washed with brine, dried over Na$_2$SO$_4$, and concentrated. The residue was purified on silica gel with a gradient of MeOH: EtOAc from 0:1 to 1:9 gave the product as a light yellow oil (195 mg, 96%). $^1$H NMR (300 MHz, CDCl$_3$): δ 9.77 (t, J=2.0 Hz, 1H), 2.60-2.38 (m, 4H), 1.80-1.52 (m, 14H), 1.46-0.98 (m, 12H).

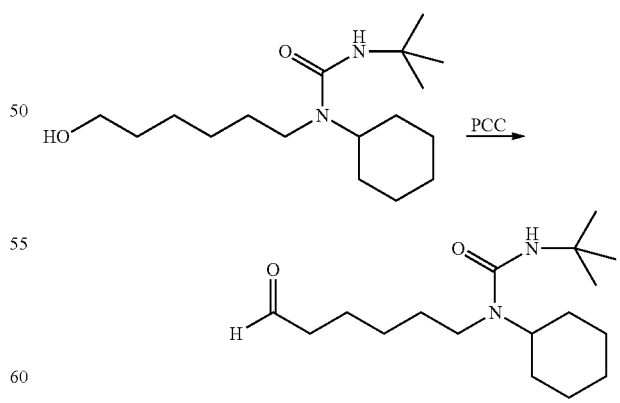

To a stirred suspension of silica gel (432 mg) in methylene chloride (10 mL) at room temperature was added 3-(tert-butyl)-1-cyclohexyl-1-(6-hydroxyhexyl)urea (400 mg, 1.34 mmol) and PCC (432 mg, 2.0 mmol). The mixture was stirred at this temperature for 2 hours, and then filtered through a pad of celite. The filtrate was concentrated and purified on silica gel column with a gradient of ethyl acetate in hexanes from 0:1 to 2:8 provided the product as a clear oil (190 mg, 48%). ¹H NMR (300 MHz, CDCl₃): δ 9.78 (t, J=1.8 Hz, 1H), 4.16 (s, 1H), 3.86-3.50 (m, 1H), 3.00 (t, J=7.9 Hz, 2H), 2.46 (td, J=7.3, 1.8 Hz, 2H), 1.87-1.46 (m, 9H), 1.46-1.20 (m, 15H), 1.20-0.95 (s, 1H).

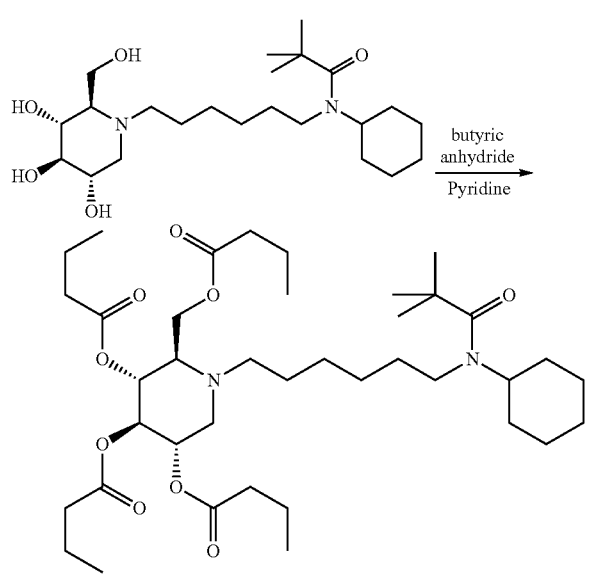

(2R,3R,4R,5S)-2-((butyryloxy)methyl)-1-(6-(N-cyclohexylpivalamido)hexyl) piperidine-3,4,5-triyl tributyrate. N-cyclohexyl-N-(6-((2R,3R,4R,5S)-3,4,5-trihydroxy-2-(hydroxymethyl)piperidin-1-yl)hexyl)pivalamide (22 mg) was dissolved in pyridine (0.5 mL) and treated with butyric anhydride (0.5 mL). The mixture was stirred at room temperature for overnight. Ethyl acetate was added to dilute the mixture and washed with saturated sodium bicarbonate, and concentrated. Purification on silica gel gave a sticky oil (35 mg, 96%). ¹H NMR (300 MHz, CDCl₃): δ 5.15-4.90 (m, 3H), 4.20-4.05 (m, 2H), 3.90-3.80 (m, 1H), 3.20-3.00 (m, 3H), 2.78-2.45 (m, 3H), 2.38-2.10 (m, 9H), 1.90-1.75 (m, 2H), 1.75-1.00 (m, 24H), 1.00-0.80 (m, 11H). Calculated MS for C₃₉H₆₈N₂O₉, 708.49; observed 709.5.

The following compounds were prepared using the methods described. The skilled practitioner will know how to substitute the appropriate reagents, starting materials and purification methods known to those skilled in the art, in order to prepare additional compounds of the present invention.

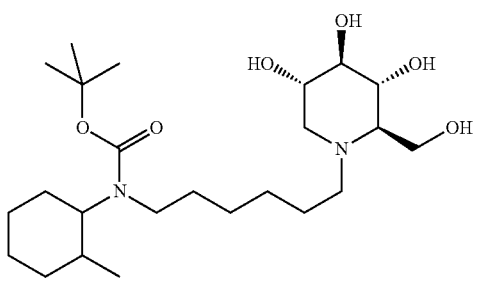 [SMILES: CC1CCCCC1N(CCCCCCN1C[C@H](O)[C@@H](O)[C@H](O)[C@H]1CO)C(=O)OC(C)(C)C]

tert-butyl(2-methylcyclohexyl)(6-((2R,3R,4R,5S)-3,4,5-trihydroxy-2-(hydroxymethyl)piperidin-1-yl)hexyl)carbamate. ¹H NMR (300 MHz, CD₃OD): δ 3.92-3.78 (m, 2H), 3.48 (td, J=10.0, 5.0 Hz, 1H), 3.35 (t, J=9.1 Hz, 1H), 3.32-3.28 (m, 1H), 3.18-3.06 (m, 2H), 3.04-2.96 (m, 2H), 2.88-2.74 (m, 1H), 2.66-2.52 (m, 1H), 2.28-2.08 (m, 2H), 1.84-1.74 (m, 2H), 1.72-1.42 (m, 7H), 1.45 (s, 9H), 1.40-1.14 (m, 7H), 1.14-0.96 (m, 1H), 0.87-0.68 (m, 3H). Calculated MS for C₂₄H₄₆N₂O₆, 458.34; observed, 459.3.

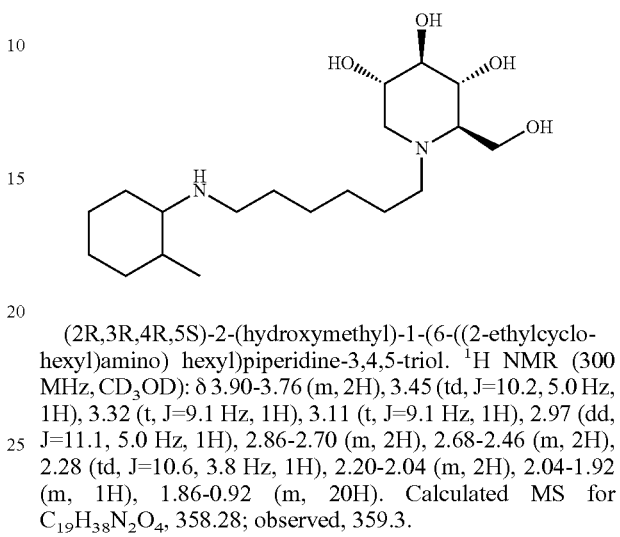

(2R,3R,4R,5S)-2-(hydroxymethyl)-1-(6-((2-ethylcyclohexyl)amino) hexyl)piperidine-3,4,5-triol. ¹H NMR (300 MHz, CD₃OD): δ 3.90-3.76 (m, 2H), 3.45 (td, J=10.2, 5.0 Hz, 1H), 3.32 (t, J=9.1 Hz, 1H), 3.11 (t, J=9.1 Hz, 1H), 2.97 (dd, J=11.1, 5.0 Hz, 1H), 2.86-2.70 (m, 2H), 2.68-2.46 (m, 2H), 2.28 (td, J=10.6, 3.8 Hz, 1H), 2.20-2.04 (m, 2H), 2.04-1.92 (m, 1H), 1.86-0.92 (m, 20H). Calculated MS for C₁₉H₃₈N₂O₄, 358.28; observed, 359.3.

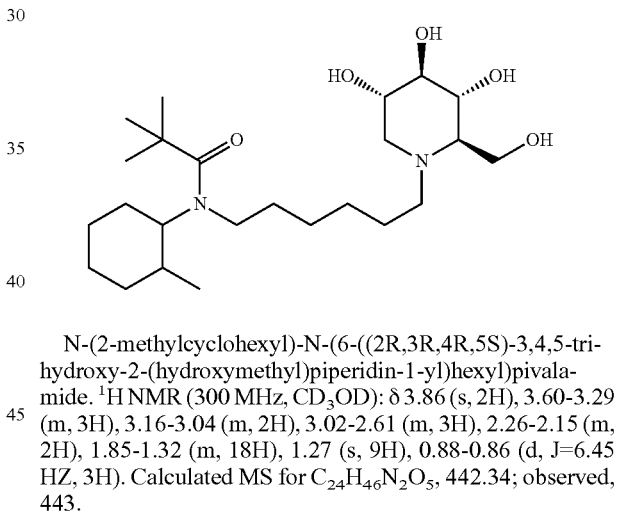

N-(2-methylcyclohexyl)-N-(6-((2R,3R,4R,5S)-3,4,5-trihydroxy-2-(hydroxymethyl)piperidin-1-yl)hexyl)pivalamide. ¹H NMR (300 MHz, CD₃OD): δ 3.86 (s, 2H), 3.60-3.29 (m, 3H), 3.16-3.04 (m, 2H), 3.02-2.61 (m, 3H), 2.26-2.15 (m, 2H), 1.85-1.32 (m, 18H), 1.27 (s, 9H), 0.88-0.86 (d, J=6.45 HZ, 3H). Calculated MS for C₂₄H₄₆N₂O₅, 442.34; observed, 443.

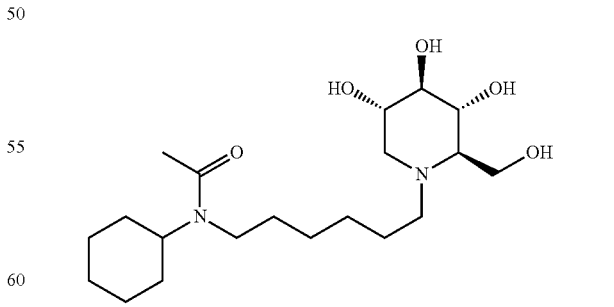

N-cyclohexyl-N-(6-((2R,3R,4R,5S)-3,4,5-trihydroxy-2-(hydroxymethyl)piperidin-1-yl)hexyl)acetamide. ¹H NMR (300 MHz, CD₃OD): δ 3.86 (m, 2H), 3.53-3.45 (m, 1H), 3.41-3.34 (m, 1H), 3.29 (s, 3H), 3.25-3.11 (m, 3H), 3.07-2.99 (m, 1H), 2.89-2.85 (m, 1H), 2.88-2.63 (m, 1H), 2.32-2.17 (m, 2H), 2.11-2.08 (m, 3H), 1.87-1.73 (m, 3H), 1.68-1.52 (m, 7H), 1.45-1.33 (m, 6H). Calculated MS for $C_{20}H_{38}N_2O_5$, 386.28; observed, 387.

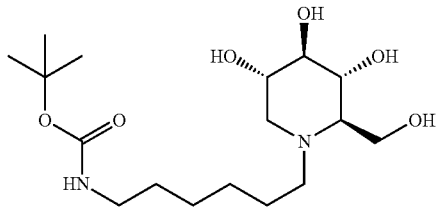 [SMILES: CC(C)(C)OC(=O)NCCCCCCN1C[C@H](O)[C@@H](O)[C@H](O)[C@H]1CO]

tert-butyl(6-((2R,3R,4R,5S)-3,4,5-trihydroxy-2-(hydroxymethyl)piperidin-1-yl)hexyl)carbamate. $^1$H NMR (300 MHz, CD$_3$OD): δ 3.85 (m, 2H), 3.46-3.43 (m, 1H), 3.38-3.37 (m, 1H), 3.15-3.09 (m, 1H), 3.04-2.96 (m, 3H), 2.85-2.76 (m, 1H), 2.63-2.53 (m, 1H), 2.22-1.93 (m, 2H), 1.49-1.47 (m, 4H), 1.42 (s, 9H), 1.33-1.32 (m, 4H). Calculated MS for $C_{17}H_{34}N_2O_6$, 362.24; observed, 363.

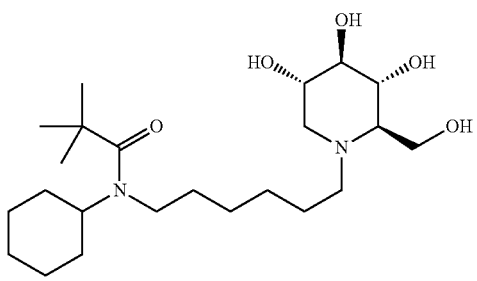 [SMILES: CC(C)(C)C(=O)N(CCCCCCN1C[C@H](O)[C@@H](O)[C@H](O)[C@H]1CO)C1CCCCC1]

N-cyclohexyl-N-(6-((2R,3R,4R,5S)-3,4,5-trihydroxy-2-(hydroxymethyl)piperidin-1-yl)hexyl)pivalamide. $^1$H NMR (300 MHz, CD$_3$OD): δ 3.90-3.86 (m, 2H), 3.51-3.44 (m, 1H), 3.39-3.30 (m, 2H), 3.16-3.10 (m, 2H), 3.04-2.98 (m, 1H), 2.83-2.78 (m, 1H), 2.66-2.59 (m, 1H), 2.25-2.15 (m, 2H), 1.93-1.84 (m, 3H), 1.70-1.32 (m, 16H), 1.26 (s, 9H). Calculated MS for $C_{23}H_{44}N_2O_5$, 428.33; observed, 429.

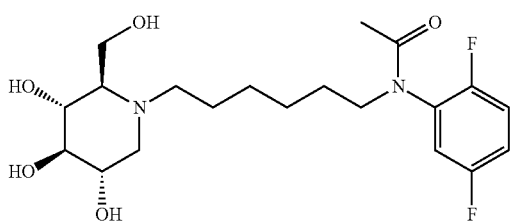

N-(2,5-difluorophenyl)-N-(6-((2R,3R,4R,5S)-3,4,5-trihydroxy-2-(hydroxylmethyl)piperidin-1-yl)hexyl)acetamide. $^1$H NMR (300 MHz, CD$_3$OD): δ 7.37-7.19 (m, 3H), 3.84 (m, 2H), 3.76-3.60 (m, 2H), 3.51-3.43 (m, 2H), 3.39-3.29b (m, 1H), 3.16-3.10 (m, 1H), 3.03-2.98 (m, 1H), 2.87-2.77 (m, 1H), 2.28-2.16 (m, 2H), 1.85 (s, 3H), 1.50-1.48 (m, 4H), 1.32-1.31 (m, 4H). Calculated MS for $C_{20}H_{30}F_2N_2O_5$, 416.21; observed, 417.

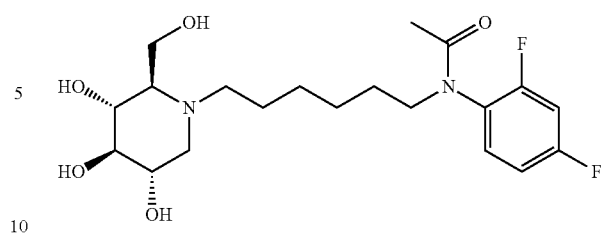

N-(2,4-difluorophenyl)-N-(6-((2R,3R,4R,5S)-3,4,5-trihydroxy-2-(hydroxylmethyl)piperidin-1-yl)hexyl)acetamide. $^1$H NMR (300 MHz, CD$_3$OD): δ 7.47-7.40 (m, 1H), 7.22-7.07 (m, 2H), 3.84-3.83 (m, 2H), 3.67-3.62 (m, 2H), 3.53-3.42 (m, 1H), 3.15-3.09 (m, 1H), 3.01-2.96 (1H), 2.80-2.75 (m, 1H), 2.62-2.57 (m, 1H), 2.28-2.12 (m, 2H), 1.93 (m, 1H), 1.81 (s, 3H), 1.49 (m, 4H), 1.31-1.30 (m, 4H). Calculated MS for $C_{20}H_{30}F_2N_2O_5$, 416.21; observed, 417.

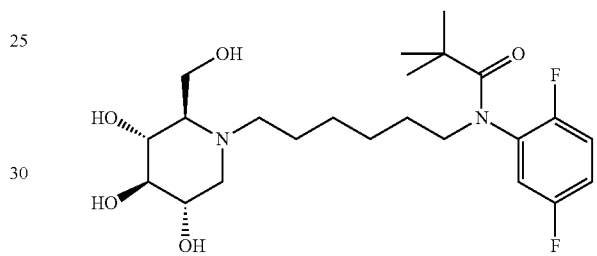

N-(2,5-difluorophenyl)-N-(6-((2R,3R,4R,5S)-3,4,5-trihydroxy-2-(hydroxylmethyl)piperidin-1-yl)hexyl)pivalamide. $^1$H NMR (300 MHz, CD$_3$OD): δ 7.32-7.18 (m, 3H), 3.83 (m, 2H), 3.57-3.51 (m, 2H), 3.49-3.29 (m, 2H), 3.15-3.09 (m, 1H), 3.01-2.96 (m, 1H), 2.84-2.75 (m, 1H), 2.62-2.52 (m, 1H), 2.22-2.11 (m, 2H), 1.56-1.46 (m, 4H), 1.31-1.30 (m, 4H), 1.06 (s, 9H). Calculated MS for $C_{23}H_{36}F_2N_2O_5$, 458.26; observed, 459.

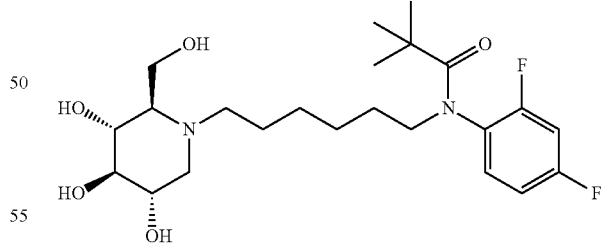

N-(2,4-difluorophenyl)-N-(6-((2R,3R,4R,5S)-3,4,5-trihydroxy-2-(hydroxylmethyl)piperidin-1-yl)hexyl)pivalamide. $^1$H NMR (300 MHz, CD$_3$OD): δ 7.46-7.38 (m, 1H), 7.18-7.03 (m, 2H), 3.84 (m, 2H), 3.51-3.29 (m, 4H), 3.19-3.10 (m, 1H), 3.06-2.97 (m, 1H), 2.87-2.77 (m, 1H), 2.64-2.54 (m, 1H), 2.49-2.14 (m, 2H), 1.53-1.50 (m, 4H), 1.40-1.29 (m, 4H), 1.25 (s, 9H). Calculated MS for $C_{23}H_{36}F_2N_2O_5$, 458.26; observed, 459.

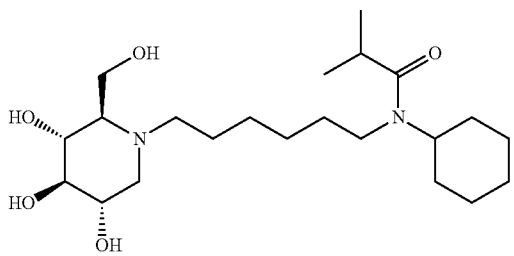 [SMILES: CC(C)C(=O)N(CCCCCCN1C[C@H](O)[C@@H](O)[C@H](O)[C@H]1CO)C1CCCCC1]

N-cyclohexyl-N-(6-((2R,3R,4R,5S)-3,4,5-trihydroxy-2-(hydroxymethyl)piperidin-1-yl)hexyl)isobutyramide. $^{1}$H NMR (300 MHz, CD$_3$OD): δ 4.24-4.14 (m, 1H), 3.86-3.82 (m, 2H), 3.74-3.66 (m, 1H), 3.51-3.44 (m, 1H), 3.25-3.19 (m, 1H), 3.16-3.11 (m, 3H), 3.05-2.95 (m, 1H), 2.93-2.75 (m, 2H), 2.67-2.55 (m, 1H), 2.27-2.13 (m, 2H), 1.93-1.79 (m, 2H), 1.70-1.36 (m, 9H), 1.33-1.19 (m, 6H), 1.18-1.07 (m, 6H). Calculated MS for C$_{22}$H$_{42}$N$_2$O$_5$, 414.31; observed, 415.

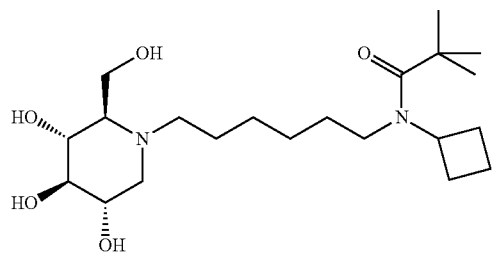

N-cyclobutyl-N-(6-((2R,3R,4R,5S)-3,4,5-trihydroxy-2-(hydroxymethyl)piperidin-1-yl)hexyl)pivalamide. $^{1}$H NMR (300 MHz, CD$_3$OD): δ 4.63 (bs, 1H), 3.86-3.85 (m, 2H), 3.52-3.44 (m, 1H), 3.40-3.30 (m, 3H), 3.17-3.11 (m, 1H), 3.05-3.00 (m, 1H), 2.89-2.79 (m, 1H), 2.67-2.58 (m, 1H), 2.27-2.16 (m, 6H), 1.76-1.34 (m, 10H), 1.26 (s, 9H). Calculated MS for C$_{21}$H$_{40}$N$_2$O$_5$, 400.29; observed, 401.

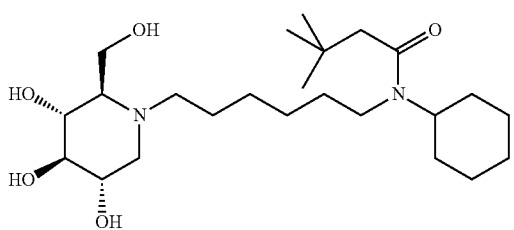 [SMILES: CC(C)(C)CC(=O)N(CCCCCCN1C[C@H](O)[C@@H](O)[C@H](O)[C@H]1CO)C1CCCCC1]

N-cyclohexyl-3,3-dimethyl-N-(6-((2R,3R,4R,5S)-3,4,5-trihydroxy-2-(hydroxymethyl)piperidin-1-yl)hexyl)butanamide. $^{1}$H NMR (300 MHz, CD$_3$OD): δ 4.87-4.18 (m, 1H), 3.94 (m, 2H), 3.89-3.31 (m, 3H), 3.15-3.06 (m, 2H), 3.01-2.88 (m, 2H), 2.81-2.73 (m, 2H), 2.34-2.31 (m, 2H), 2.24 (s, 2H), 1.93-1.14 (m, 17H), 1.04 (s, 9H). Calculated MS for C$_{24}$H$_{46}$N$_2$O$_5$, 442.34; observed, 443.

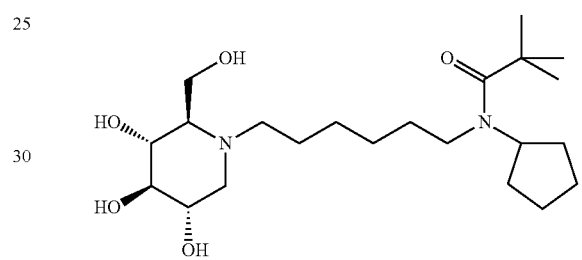

N-cyclopentyl-N-(6-((2R,3R,4R,5S)-3,4,5-trihydroxy-2-(hydroxymethyl)piperidin-1-yl)hexyl)pivalamide. $^{1}$H NMR (300 MHz, CD$_3$OD): δ 4.49 (m, 1H), 3.89-3.80 (m, 2H), 3.51-3.43 (m, 1H), 3.38-3.31 (m, 2H), 3.01-2.96 (m, 1H), 2.84-2.75 (m, 1H), 2.62-2.53 (m, 1H), 2.10 (m, 2H), 1.89-1.31 (m, 18), 1.26 (m, 9H). Calculated MS for C$_{22}$H$_{42}$N$_2$O$_5$, 414.31; observed, 415.

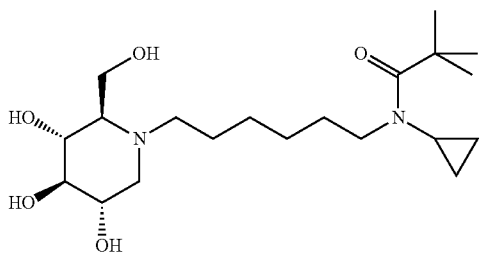 [SMILES: CC(C)(C)C(=O)N(CCCCCCN1C[C@H](O)[C@@H](O)[C@H](O)[C@H]1CO)C1CC1]

N-cyclopropyl-N-(6-((2R,3R,4R,5S)-3,4,5-trihydroxy-2-(hydroxyl methyl)piperidin-1-yl)hexyl)pivalamide. $^{1}$H NMR (300 MHz, CD$_3$OD): δ 3.87 (m, 2H), 3.54-3.47 (m, 1H), 3.41-3.30 (m, 3H), 3.30-3.29 (m, 2H), 3.19-3.13 (m, 1H), 3.08-3.03 (m, 1H), 2.93-2.61 (m, 3H), 2.32-2.24 (m, 2H), 1.61-1.50 (m, 4H), 1.36-1.30 (m, 4H), 1.29 (s, 9H), 0.91-0.86 (m, 2H), 0.68-0.67 (m, 2H). Calculated MS for C$_{20}$H$_{38}$N$_2$O$_5$, 386.28; observed, 387.

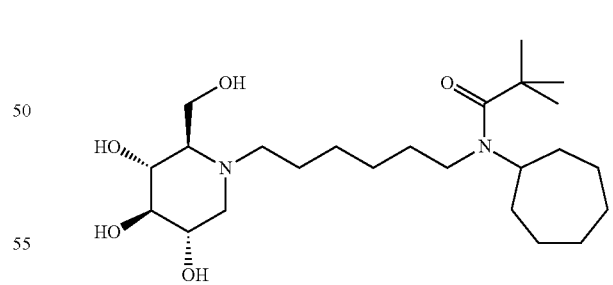

N-cycloheptyl-N-(6-((2R,3R,4R,5S)-3,4,5-trihydroxy-2-(hydroxymethyl)piperidin-1-yl)hexyl)pivalamide. $^{1}$H NMR (300 MHz, CD$_3$OD): δ 4.18-4.00 (m, 2), 3.92-3.88 (m, 1H), 3.75-3.48 (m, 2H), 3.42-3.28 (m, 3H), 3.21-3.01 (m, 3H), 2.95-2.75 (m, 2H), 1.90-1.66 (m, 8H), 1.65-1.45 (m, 8H), 1.43-1.35 (m, 4H), 1.26 (s, 9H). Calculated MS for C$_{24}$H$_{46}$N$_2$O$_5$, 442.34; observed, 443.

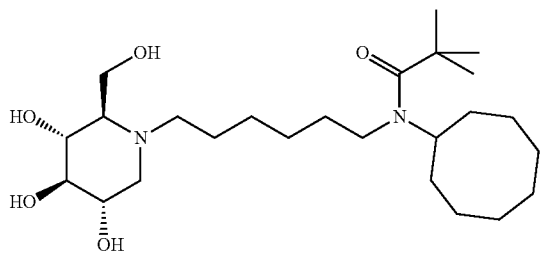 [SMILES: CC(C)(C)C(=O)N(CCCCCCN1C[C@H](O)[C@@H](O)[C@H](O)[C@H]1CO)C1CCCCCCC1]

N-cyclooctyl-N-(6-((2R,3R,4R,5S)-3,4,5-trihydroxy-2-(hydroxymethyl)piperidin-1-yl)hexyl)pivalamide. $^1$H NMR (300 MHz, CD$_3$OD): δ 3.86-3.85 (m, 2H), 3.52-3.44 (m, 1H), 3.39-3.33 (m, 1H), 3.24-2.99 (m, 4H), 2.89-2.80 (m, 1H), 2.68-2.63 (m, 1H), 2.28-2.17 (m, 2H), 1.93-1.24 (m, 23H), 1.21 (s, 9H). Calculated MS for C$_{25}$H$_{48}$N$_2$O$_5$, 456.36; observed, 457.

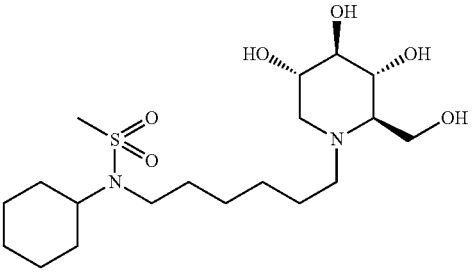

N-cyclohexyl-N-(6-(((2R,3R,4R,5S)-3,4,5-trihydroxy-2-(hydroxymethyl)piperidin-1-yl)hexyl)methanesulfonamide. $^1$H NMR (300 MHz, CD$_3$OD): δ 3.85 (m, 2H), 3.57-3.43 (m, 2H), 3.38-3.29 (m, 3H), 3.16-3.10 (m, 3H), 3.03-2.97 (m, 1H), 2.87 (s, 3H), 2.85-2.77 (m, 1H), 2.65-2.56 (m, 1H), 2.24-2.13 (m, 2H), 1.84-1.80 (m, 4H), 1.65-1.45 (m, 7H), 1.42-1.33 (m, 3H), 1.21-1.11 (m, 1H). Calculated MS for C$_{19}$H$_{38}$N$_2$O$_6$S, 422.25; observed, 423.

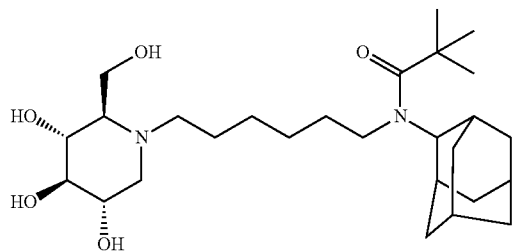 [SMILES: CC(C)(C)C(=O)N(CCCCCCN1C[C@H](O)[C@@H](O)[C@H](O)[C@H]1CO)C1C2CC3CC(C2)CC1C3]

N-((1R,5R,7S)-adamantan-2-yl)-N-(6-((2R,3R,4R,5S)-3,4,5-trihydroxy-2-(hydroxylmethyl)piperidin-1-yl)hexyl)pivalamide. $^1$H NMR (300 MHz, CD$_3$OD): δ 3.90-3.85 (m, 2H), 3.55-3.43 (m, 2H), 3.38-3.35 (m, 1H), 3.16-3.10 (m, 1H), 3.03-2.98 (m, 1H), 2.83-2.78 (m, 1H), 2.62-2.57 (m, 1H), 2.25-2.17 (m, 2H), 2.15-2.01 (1H), 1.89-1.79 (m, 5H), 1.69-1.65 (m, 4H), 1.49-1.29 (m, 4H), 1.28 (s, 9H). Calculated MS for C$_{27}$H$_{48}$N$_2$O$_5$, 480.36; observed, 481.

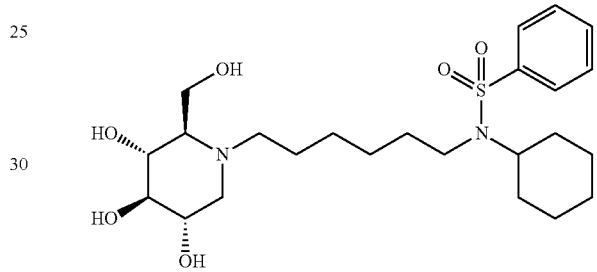

N-cyclohexyl-N-(6-(((2R,3R,4R,5S)-3,4,5-trihydroxy-2-(hydroxymethyl)piperidin-1-yl)hexyl)benzenesulfonamide. $^1$H NMR (300 MHz, CD$_3$OD): δ 7.84-7.81 (m, 2H), 7.64-7.53 (m, 3H), 3.90-3.80 (m, 2H), 3.62-3.34 (m, 3H), 3.18-3.07 (m, 3H), 3.01-2.96 (m, 1H), 2.85-2.75 (m, 1H), 2.63-2.53 (m, 1H), 2.21-2.06 (m, 2H), 1.93-1.09 (m, 18H). Calculated MS for C$_{24}$H$_{40}$N$_2$O$_6$S, 484.26; observed, 485.

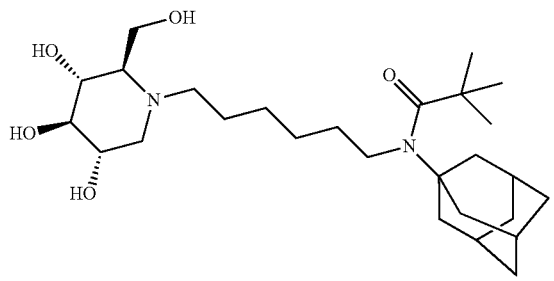 [SMILES: CC(C)(C)C(=O)N(CCCCCCN1C[C@H](O)[C@@H](O)[C@H](O)[C@H]1CO)C12CC3CC(CC(C3)C1)C2]

N-((3S,5S,7S)-adamantan-1-yl)-N-(6-((2R,3R,4R,5S)-3,4,5-trihydroxy-2-(hydroxymethyl)piperidin-1-yl)hexyl)pivalamide. $^1$H NMR (300 MHz, CD$_3$OD): δ 3.85 (m, 2H), 3.50-3.44 (m, 1H), 3.23-3.08 (m, 1H), 3.01-2.97 (m, 1H), 2.81-2.79 (m, 1H), 2.60-2.57 (m, 1H), 2.26-1.32 (m, 18H), 1.18 (s, 9H). Calculated MS for C$_{27}$H$_{48}$N$_2$O$_5$, 480.36; observed, 481.

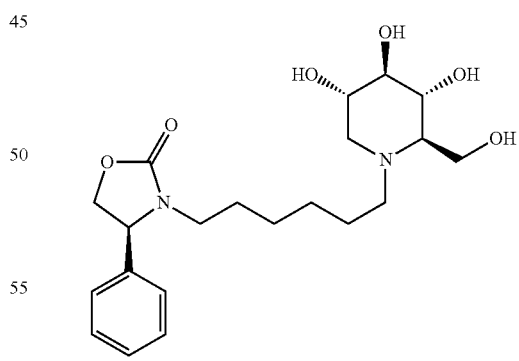

(S)-4-phenyl-3-(6-((2R,3R,4R,5S)-3,4,5-trihydroxy-2-(hydroxymethyl)piperidin-1-yl)hexyl)oxazolidin-2-one. $^1$H NMR (300 MHz, CD$_3$OD): δ 7.47-7.34 (m, 5H), 4.96-4.91 (m, 1H), 4.71-4.65 (m, 1H), 4.16-4.11 (m, 1H), 3.84-3.83 (m, 2H), 3.52-3.42 (m, 1H), 3.40-3.29 (m, 2H), 3.15-3.12 (m, 1H), 2.99-2.94 (m 1H), 2.84-2.72 (m, 2H), 2.59-2.53 (m, 1H), 2.20-2.10 (m, 2H), 1.46-1.39 (m 4H), 1.26-1.25 (m, 4H). Calculated MS for C$_{21}$H$_{32}$N$_2$O$_6$, 408.23; observed, 409.

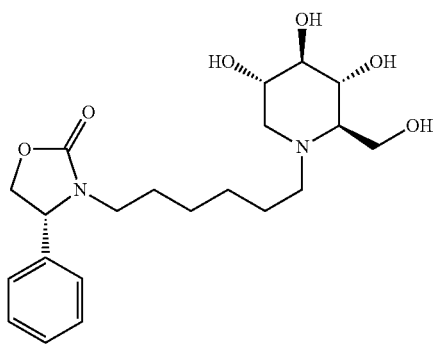 [SMILES: O=C1OC[C@@H](c2ccccc2)N1CCCCCCN1C[C@H](O)[C@@H](O)[C@H](O)[C@H]1CO]

(R)-4-phenyl-3-(6-((2R,3R,4R,5S)-3,4,5-trihydroxy-2-(hydroxymethyl)piperidin-1-yl)hexyl)oxazolidin-2-one. ¹H NMR (300 MHz, CD₃OD): δ 7.47-7.34 (m, 5H), 4.96-4.91 (m, 1H), 4.71-4.65 (m, 1H), 4.17-4.12 (m, 1H), 3.84-3.82 (m, 2H), 3.51-3.42 (m, 1H), 3.31-3.29 (m, 2H), 3.16-3.10 (m, 1H), 3.01-2.96 (m, 1H), 2.84-2.74 (m, 2H), 2.61-2.54 (m, 1H), 2.23-2.13 (m, 2H), 1.46-1.44 (m, 4H), 1.31-1.26 (m, 4H). Calculated MS for C₂₁H₃₂N₂O₆, 408.23; observed, 409.

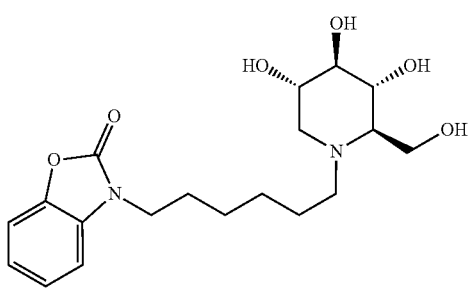 [SMILES: O=c1oc2ccccc2n1CCCCCCN1C[C@H](O)[C@@H](O)[C@H](O)[C@H]1CO]

3-(6-((2R,3R,4R,5S)-3,4,5-trihydroxy-2-(hydroxymethyl)piperidin-1-yl)hexyl)benzo[d]oxazol-2(3H)-one. ¹H NMR (300 MHz, CD₃OD): δ 7.25-7.10 (m, 4H), 4.87-3.80 (m, 4H), 3.51-3.43 (m, 1H), 3.37-3.33 (m, 1H), 3.16-3.10 (m, 1H), 2.99-2.95 (m, 1H), 2.84-2.74 (m, 1H), 2.61-2.52 (m, 1H), 2.20-2.10 (m, 2H), 1.82-1.72 (m, 2H), 1.53-1.36 (m, 6H). Calculated MS for C₁₉H₂₈N₂O₆, 380.19; observed, 381.

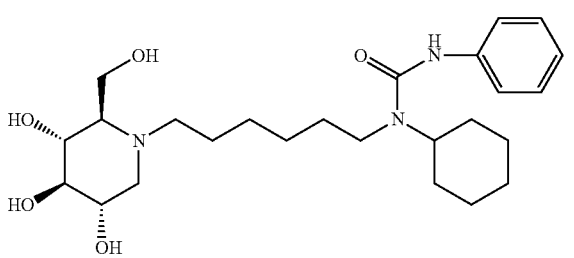 [SMILES: O=C(Nc1ccccc1)N(CCCCCCN1C[C@H](O)[C@@H](O)[C@H](O)[C@H]1CO)C1CCCCC1]

1-cyclohexyl-3-phenyl-1-(6-((2R,3R,4R,5S)-3,4,5-trihydroxy-2-(hydroxylmethyl)piperidin-1-yl)hexyl)urea. ¹H NMR (300 MHz, CD₃OD): δ 7.34-7.23 (m, 4H), 7.03-6.99 (m, 1H), 3.89-3.80 (m, 2H), 3.54-3.42 (m, 1H), 3.24-3.23 (m, 2H), 3.14-3.08 (m, 1H), 2.99-2.95 (m, 1H), 2.80-2.75 (m, 1H), 2.61-2.56 (m, 1H), 2.19-2.07 (m, 2H), 1.87-1.75 (m, 4H), 1.65-1.35 (m, 16H). Calculated MS for C₂₅H₄₁N₃O₅, 463.30; observed, 464.

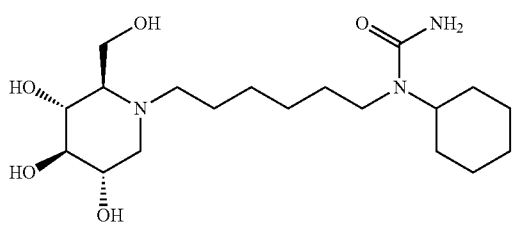 [SMILES: NC(=O)N(CCCCCCN1C[C@H](O)[C@@H](O)[C@H](O)[C@H]1CO)C1CCCCC1]

1-cyclohexyl-1-(6-((2R,3R,4R,5S)-3,4,5-trihydroxy-2-(hydroxymethyl)piperidin-1-yl)hexyl)urea. ¹H NMR (300 MHz, CD₃OD): δ 3.86-3.84 (m, 2H), 3.51-3.43 (m, 1H), 3.15-3.07 (m, 3H), 3.02-2.97 (m, 1H), 2.84-2.77 (m, 1H), 2.63-2.54 (m, 1H), 2.22-2.11 (m, 2H), 1.83-1.79 (m, 2H), 1.72-1.62 (m, 2H), 1.53-1.32 (m, 18H). Calculated MS for C₁₉H₃₇N₃O₅, 387.27; observed, 388.

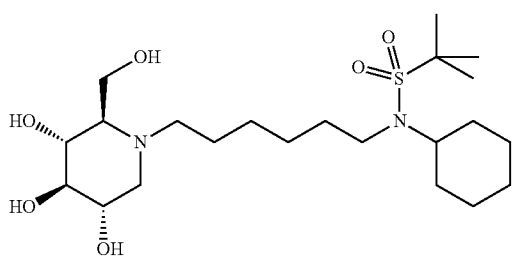 [SMILES: CC(C)(C)S(=O)(=O)N(CCCCCCN1C[C@H](O)[C@@H](O)[C@H](O)[C@H]1CO)C1CCCCC1]

N-cyclohexyl-2-methyl-N-(6-((2R,3R,4R,5S)-3,4,5-trihydroxy-2-(hydroxylmethyl)piperidin-1-yl)hexyl)propane-2-sulfonamide. ¹H NMR (300 MHz, CD₃OD): δ 3.92-3.78 (m, 2H), 3.54-3.40 (m, 2H), 3.40-3.28 (m, 1H), 3.22 (t, J=7.6 Hz, 2H), 3.12 (t, J=8.8 Hz, 1H), 2.95 (dd, J=11.4, 4.7 Hz, 1H), 2.88-2.72 (m, 1H), 2.66-2.50 (m, 1H), 2.25-2.07 (m, 2H), 1.98-1.76 (m, 4H), 1.72-1.42 (m, 7H), 1.42-1.24 (m, 15H), 1.24-1.04 (m, 1H). Calculated MS for C₂₂H₄₄N₂O₆S, 464.29; observed, 465.3.

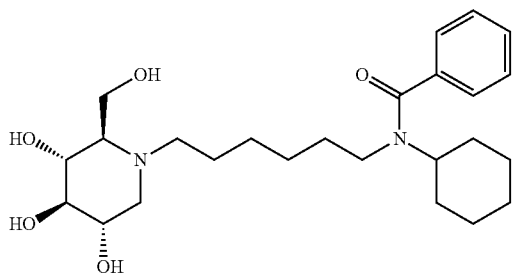 [SMILES: O=C(c1ccccc1)N(CCCCCCN1C[C@H](O)[C@@H](O)[C@H](O)[C@H]1CO)C1CCCCC1]

N-cyclohexyl-N-(6-((2R,3R,4R,5S)-3,4,5-trihydroxy-2-(hydroxymethyl)piperidin-1-yl)hexyl)benzamide. ¹H NMR (300 MHz, CD₃OD): δ 7.50-7.42 (m, 3H), 7.37-7.29 (m, 2H), 3.90-3.75 (m, 2H), 3.60-3.30 (m, 4H), 3.22-2.98 (m, 3H), 2.98-2.76 (m, 1H), 2.76-2.38 (m, 1H), 2.38-2.02 (m, 2H), 1.95-1.80 (m, 1H), 1.80-1.62 (m, 6H), 1.62-1.48 (m, 3H), 1.48-1.22 (m, 5H), 1.14-0.90 (m, 3H). Calculated MS for C₂₅H₄₀N₂O₅, 448.29, 464.29; observed, 449.3.

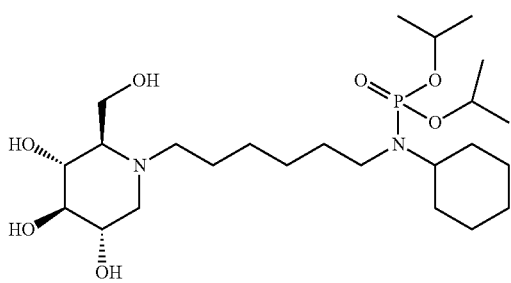 [SMILES: CC(C)OP(=O)(OC(C)C)N(CCCCCCN1C[C@H](O)[C@@H](O)[C@H](O)[C@H]1CO)C1CCCCC1]

diisopropyl cyclohexyl(6-((2R,3R,4R,5S)-3,4,5-trihydroxy-2-(hydroxymethyl)piperidin-1-yl)hexyl)phosphoramidate. $^1$H NMR (300 MHz, CD$_3$OD): δ 4.56-4.42 (m, 2H), 3.87 (d, J=2.3 Hz, 2H), 3.49 (td, J=10.3, 4.7 Hz, 1H), 3.42-3.10 (m, 1H), 3.20-3.00 (m, 3H), 3.00-2.80 (m, 3H), 2.74-2.60 (m, 1H), 1.88-1.70 (m, 4H), 1.70-1.44 (m, 7H), 1.44-1.20 (m, 18H), 1.20-1.00 (m, 1H). Calculated MS for C$_{24}$H$_{49}$N$_2$O$_7$P, 508.33; observed, 509.3.

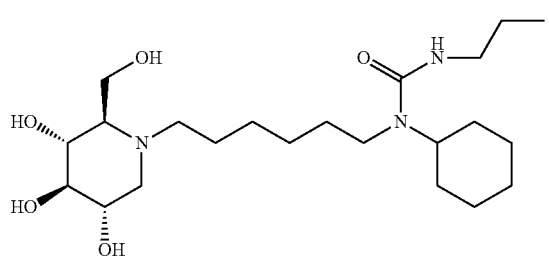 [SMILES: CCCNC(=O)N(CCCCCCN1C[C@H](O)[C@@H](O)[C@H](O)[C@H]1CO)C1CCCCC1]

1-cyclohexyl-3-propyl-1-(6-((2R,3R,4R,5S)-3,4,5-trihydroxy-2-(hydroxymethyl)piperidin-1-yl)hexyl)urea. $^1$H NMR (300 MHz, CD$_3$OD): δ 3.92-3.78 (m, 3H), 3.52-3.42 (m, 1H), 3.40-3.32 (m, 1H), 3.18-2.96 (m, 6H), 2.88-2.76 (m, 1H), 2.66-2.54 (m, 1H), 2.24-2.10 (m, 2H), 1.86-1.74 (m, 2H), 1.74-1.59 (m, 3H), 1.59-1.44 (m, 7H), 1.44-1.26 (m, 7H), 1.22-1.06 (m, 1H), 10.90 (t, J=7.3 Hz, 3H). Calculated MS for C$_{22}$H$_{43}$N$_3$O$_5$, 429.32; observed, 430.4.

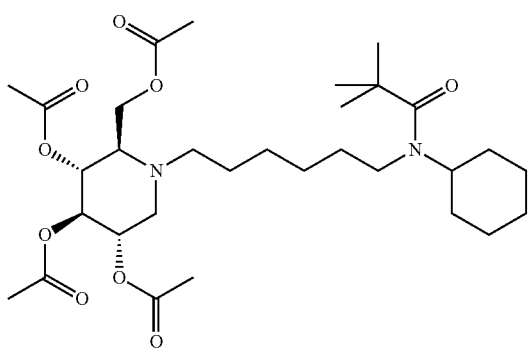 [SMILES: CC(=O)OC[C@@H]1[C@@H](OC(C)=O)[C@H](OC(C)=O)[C@@H](OC(C)=O)CN1CCCCCCN(C(=O)C(C)(C)C)C1CCCCC1]

(2R,3R,4R,5S)-2-(acetoxymethyl)-1-(6-(N-cyclohexylpivalamido)hexyl)piperidine-3,4,5-triyl triacetate. $^1$H NMR (300 MHz, CDCl$_3$): δ 5.10-4.88 (m, 3H), 4.12 (d, J=2.3 Hz, 2H), 3.88-3.74 (m, 1H), 3.15 (dd, J=11.7, 5.0 Hz, 1H), 3.10-2.96 (m, 2H), 2.76-2.46 (m, 3H), 2.30 (t, J=10.3 Hz, 1H), 2.04 (s, 3H), 1.99 (s, 6H), 1.98 (s, 3H), 1.88-1.74 (m, 2H), 1.72-1.58 (m, 3H), 1.58-1.16 (m, 21H), 1.16-1.00 (m, 1H). Calculated MS for C$_{31}$H$_{52}$N$_2$O$_9$, 596.37; observed, 597.4.

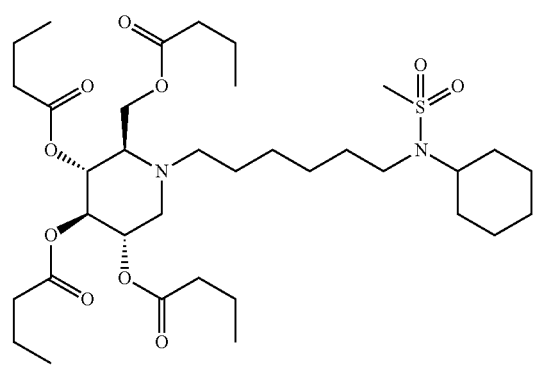 [SMILES: CCCC(=O)OC[C@@H]1[C@@H](OC(=O)CCC)[C@H](OC(=O)CCC)[C@@H](OC(=O)CCC)CN1CCCCCCN(C1CCCCC1)S(C)(=O)=O]

(2R,3R,4R,5S)-2-((butyryloxy)methyl)-1-(6-(N-cyclohexylmethyl sulfonamido)hexyl)piperidine-3,4,5-triyl tributyrate. $^1$H NMR (300 MHz, CDCl$_3$): δ 5.18-4.90 (m, 3H), 4.24-4.04 (m, 2H), 3.64-3.50 (m, 1H), 3.18 (dd, J=11.7, 5.3 Hz, 1H), 3.13-3.02 (m, 2H), 2.84 (s, 3H), 2.80-2.45 (m, 3H), 2.38-2.15 (m, 9H), 1.89-1.76 (m, 4H), 1.70-1.20 (m, 22H), 1.18-1.04 (m, 1H), 1.00-0.86 (m, 11H). Calculated MS for C$_{35}$H$_{62}$N$_2$O$_{10}$S, 702.41; observed, 703.4.

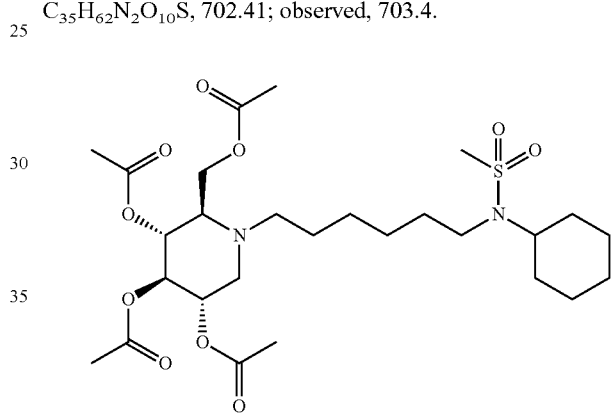

(2R,3R,4R,5S)-2-(acetoxymethyl)-1-(6-(N-cyclohexylmethylsulfonamido)hexyl)piperidine-3,4,5-triyl triacetate. $^1$H NMR (300 MHz, CDCl$_3$): δ 5.14-4.91 (m, 3H), 4.22-4.08 (m, 2H), 3.64-3.50 (m, 1H), 3.19 (dd, J=11.4, 5.0 Hz, 1H), 3.14-3.03 (m, 2H), 2.84 (s, 3H), 2.80-2.67 (m, 1H), 2.67-2.48 (m, 2H), 2.32 (t, J=5.3 Hz, 1H), 2.09 (s, 3H), 2.04 (s, 6H), 2.03 (s, 3H), 1.90-1.75 (m, 4H), 1.72-1.50 (m, 4H), 1.50-1.18 (m, 9H), 1.18-1.00 (m, 1H). Calculated MS for C$_{27}$H$_{46}$N$_2$O$_{10}$S, 590.29; observed, 591.3.

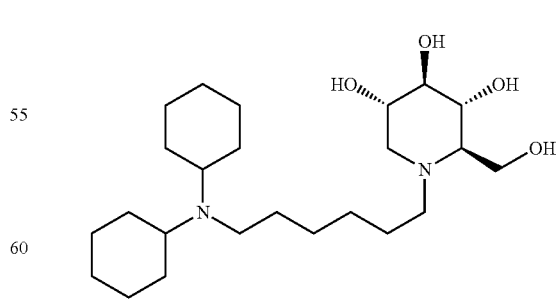

(2R,3R,4R,5S)-1-(6-(dicyclohexylamino)hexyl)-2-(hydroxymethyl)piperidine-3,4,5-triol. $^1$H NMR (300 MHz, CD$_3$OD): δ 3.94-3.80 (m, 2H), 3.55-3.41 (m, 1H), 3.41-3.33 (m, 1H), 3.20-3.08 (m, 3H), 3.05-2.94 (m, 1H), 2.91-2.76 (m, 1H), 2.64-2.50 (m, 1H), 2.23-2.10 (m, 2H), 2.10-1.98 (m, 2H), 1.78-1.63 (m, 6H), 1.63-1.10 (m, 21H), 0.95-0.82 (m, 1H). Calculated MS for $C_{24}H_{46}N_2O_4$, 426.35; observed, 427.28.

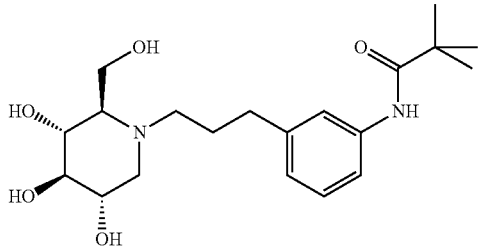 [SMILES: CC(C)(C)C(=O)Nc1cccc(CCCN2C[C@H](O)[C@@H](O)[C@H](O)[C@H]2CO)c1]

N-(3-(3-((2R,3R,4R,5S)-3,4,5-trihydroxy-2-(hydroxymethyl)piperidin-1-yl)propyl)phenyl)pivalamide. $^1$H NMR (300 MHz, CD$_3$OD): δ 7.46 (s, 1H), 7.34-7.20 (m, 2H), 7.02-6.96 (m 1H), 4.78 (s, 1H), 3.98-3.88 (m, 1H), 3.84-3.76 (m, 1H), 3.64-3.52 (m, 1H), 3.52-3.40 (m, 1H), 3.28-3.04 (m, 3H), 3.04-2.82 (m, 1H), 2.76-2.50 (m, 4H), 2.04-1.90 (m, 2H), 1.30 (s, 9H). Calculated MS for $C_{20}H_{32}N_2O_5$, 380.23; observed, 381.0.

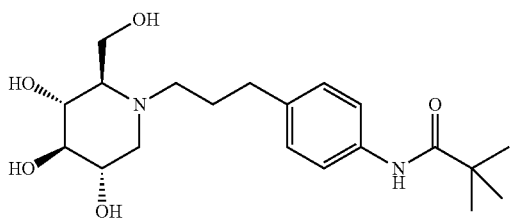

N-(4-(3-((2R,3R,4R,5S)-3,4,5-trihydroxy-2-(hydroxymethyl)piperidin-1-yl)propyl)phenyl)pivalamide. $^1$H NMR (300 MHz, CD$_3$OD): δ 7.48-7.41 (m, 2H), 7.22-7.15 (m, 2H), 4.78 (s, 1H), 3.98-3.88 (m, 1H), 3.84-3.72 (m, 1H), 3.62-3.51 (m, 1H), 3.51-3.40 (m, 1H), 3.28-3.02 (m, 3H), 3.02-2.82 (m, 1H), 2.74-2.50 (m, 4H), 2.04-1.90 (m, 2H), 1.30 (s, 9H). Calculated MS for $C_{20}H_{32}N_2O_5$, 380.23; observed, 381.0.

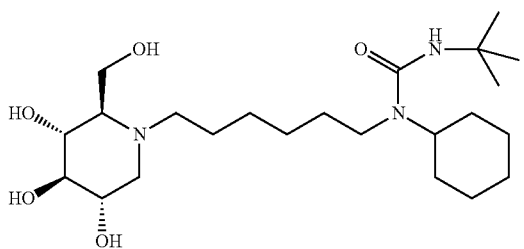 [SMILES: CC(C)(C)NC(=O)N(CCCCCCN1C[C@H](O)[C@@H](O)[C@H](O)[C@H]1CO)C1CCCCC1]

3-(tert-butyl)-1-cyclohexyl-1-(6-((2R,3R,4R,5S)-3,4,5-trihydroxy-2-(hydroxymethyl)piperidin-1-yl)hexyl)urea. $^1$H NMR (300 MHz, CD3OD): δ 5.01 (s, 1H), 3.94-3.78 (m, 3H), 3.52-3.40 (m, 1H), 3.40-3.32 (m, 1H), 3.18-2.94 (m, 4H), 2.88-2.74 (m, 1H), 2.66-2.52 (m, 1H), 2.24-2.06 (m, 2H), 1.89-1.74 (m, 2H), 1.74-1.58 (m, 3H), 1.58-1.45 (m, 4H), 1.45-1.24 (m, 17H), 1.22-1.04 (m, 1H). Calculated MS for $C_{23}H_{45}N_3O_5$, 443.34; observed, 444.3.

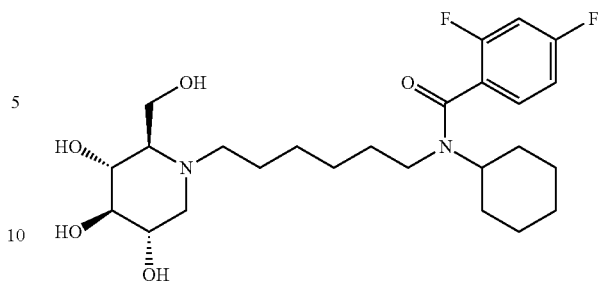

N-cyclohexyl-2,4-difluoro-N-(6-((2R,3R,4R,5S)-3,4,5-trihydroxy-2-(hydroxymethyl)piperidin-1-yl)hexyl)benzamide. $^1$H NMR (300 MHz, CD$_3$OD): δ 7.44-7.30 (m, 1H), 7.14-7.02 (m 2H), 3.90-3.78 (m, 2H), 3.55-3.32 (m, 3H), 3.20-2.40 (m, 6H), 2.25-2.00 (m, 2H), 1.93-1.24 (m, 16H), 1.24-0.94 (m, 2H). Calculated MS for $C_{25}H_{38}F_2N_2O_5$, 484.27; observed, 485.3.

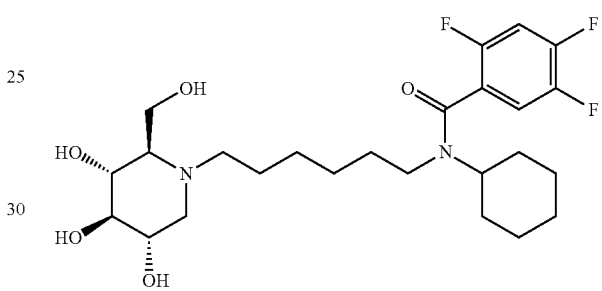

N-cyclohexyl-2,4,5-trifluoro-N-(6-((2R,3R,4R,5S)-3,4,5-trihydroxy-2-(hydroxymethyl)piperidin-1-yl)hexyl)benzamide. $^1$H NMR (300 MHz, D$_2$O): δ 7.44-7.27 (m, 2H), 3.90-3.78 (m, 2H), 3.56-3.32 (m, 3H), 3.20-3.08 (m, 2H), 3.06-2.90 (m, 1H), 2.90-2.70 (m, 1H), 2.70-2.54 (m, 1H), 2.54-2.36 (m, 1H), 2.28-2.06 (m, 2H), 1.93-1.50 (m, 11H), 1.50-1.26 (m, 4H), 1.18-0.94 (m, 3H). Calculated MS for $C_{25}H_{37}F_3N_2O_5$, 502.27; observed, 503.3.

FORMULATIONS

The present invention also relates to compositions or formulations which comprise the glucosidase inhibitors according to the present invention. In general, the compositions of the present invention comprise an effective amount of one or more alkylated imino sugars and salts thereof according to the present invention which are effective for providing glucosidase inhibition; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known anti-viral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, pre-filled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more alkylated imino sugars according to the present invention and one or more excipients; from about 0.01 mg to about 100 mg of one or more alkylated imino sugars according to the present invention and one or more excipients; and from about 0.1 mg to about 10 mg of one or more alkylated imino sugars according to the present invention; and one or more excipients.

PROCEDURES

The following procedures can be utilized in evaluating and selecting compounds as glucosidase inhibitors.

Cells and viruses: BVDV free MDBK cells (CCL 22) were obtained from the American Type Culture Collection and propagated in DMEMIF12 essential medium supplemented with penicillin (500 U/ml), streptomycin (500 U/ml), and 10% heat inactivated horse serum (Invitrogen). Cells were maintained in a humidified incubator at 37° C. with 5% $CO_2$. BVDV (NADL strain). For infections, virus inoculum was added in complete medium and adsorbed for 1 hour at 37° C., the inoculum was then removed, the cells washed once with medium and fresh medium containing compounds added. Virus stocks were prepared by freeze thawing the infected cells and culture supernatant three times followed by centrifugation at 1,000 g for 5 min., Stock titers were determined, and stocks were aliquoted and stored at −80° C. WNV was obtained from a eDNA clone of a human 2002 isolate from Texas; virus obtained from BHK cells electroporated with the in vitro synthesized RNA from this eDNA clone was passaged in Vero cells before use in antiviral assays. Dengue virus (DV) serotype 2 was a New Guinea C virus that had been passaged 28 times in suckling mouse brain, twice in Vero cells, and once in C6/36 mosquito cells.

BVDV antiviral and plaque assays: To evaluate antiviral activity against BVDV, a single cycle virus yield reduction assay was performed in the presence of from 0.16 µM to 100 µM through 5-fold dilution. Specifically, 2×105 MDBK cells/well were plated in 24 well plates. Twenty four hours later, the cells were infected with BVDV at multiplicity of infection (MOI) of 0.5 PFU/cell in 100 uL complete media. After adsorption for 1 hour at 37° C., the inoculum was removed, and cells were washed with media before media containing vehicle or from 0.16 µM to 100 µM through 5-fold dilution of test compound was added. At 22 hours post infection, both cells and media were collected and freeze-thawed three times before the virus was tittered. For BVDV virus, titer determination, $10^{-2}$, $10^{-3}$, $10^{-4}$ dilutions of virus were inoculated onto MDBK cells as described previously. After absorption and washing the cells were overlaid with medium containing methylcellulose or soft agar and incubated at 37° C. for 3 days or until plaques were visible. Plaques were counted directly under the microscope or after staining with crystal violet in 70% methanol for 15 minutes.

Toxicity Assay (Sigma, St. Louis, Mo.). Briefly, cells cultured under conditions identical to those used in the viral assay were incubated with 0.16 µM to 100 µM through 5-fold dilution of the compound for 22 hours. (3-(4,5-Dimethylthiazol-2-yl)-2,5-diphenyltetrazolium bromide, a yellow tetrazole) was added to the media to a final concentration of 0.5 mg/ml and was incubated for 3 hours at 37° C. After the culture media was removed, formazan crystals was dissolved by adding 150 ul of solubilization solution (10% Triton X-100, 0.1 N HCl in anhydrous isopropanol) for 15-30 minutes. The absorbance of the dissolved formazan was measured spectrophotometrically at 570 nm with absorbance at 690 nm as background.

TABLE 3

Examples of Alkylated Imino Sugar Compounds and their Potencies for Biological Activity

| Entry | Structure | BVDV $EC_{50}$ | BVDV $EC_{90}$ | $CC_{50}$ |
|---|---|---|---|---|
| 1 | 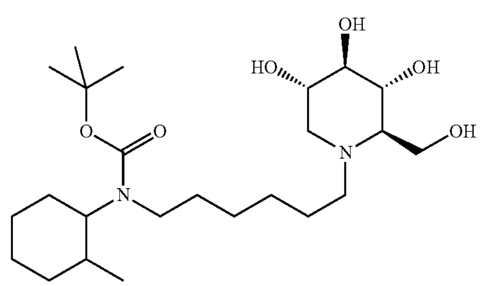 [SMILES: CC1CCCCC1N(CCCCCCN1C[C@H](O)[C@@H](O)[C@H](O)[C@H]1CO)C(=O)OC(C)(C)C] | 0.4 | 3.5 | 250 |
| 2 | 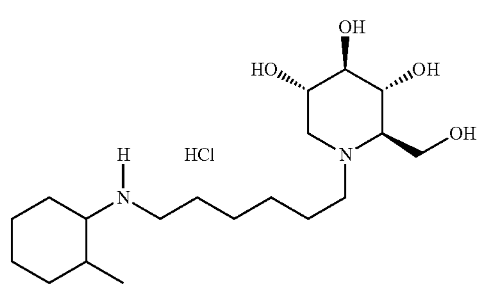 [SMILES: CC1CCCCC1NCCCCCCN1C[C@H](O)[C@@H](O)[C@H](O)[C@H]1CO ; Cl] | 100 | 100 | >500 |
| 3 | 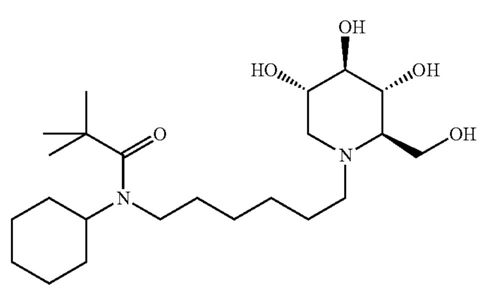 [SMILES: CC(C)(C)C(=O)N(CCCCCCN1C[C@H](O)[C@@H](O)[C@H](O)[C@H]1CO)C1CCCCC1] | 0.2 | 13 | >500 |

TABLE 3-continued

Examples of Alkylated Imino Sugar Compounds and their Potencies for Biological Activity

| Entry | Structure | BVDV EC$_{50}$ | BVDV EC$_{90}$ | CC$_{50}$ |
|---|---|---|---|---|
| 4 | 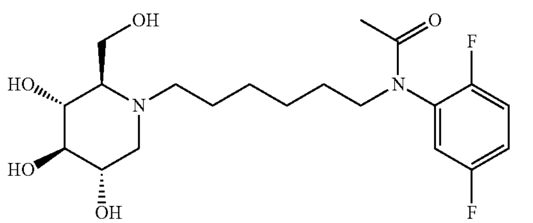 [SMILES: CC(=O)N(CCCCCCN1C[C@H](O)[C@@H](O)[C@H](O)[C@H]1CO)c1cc(F)ccc1F] | 5 | 100 | >500 |
| 5 | 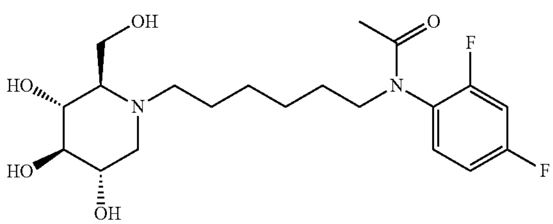 [SMILES: CC(=O)N(CCCCCCN1C[C@H](O)[C@@H](O)[C@H](O)[C@H]1CO)c1ccc(F)cc1F] | 6 | 67 | >500 |
| 6 | 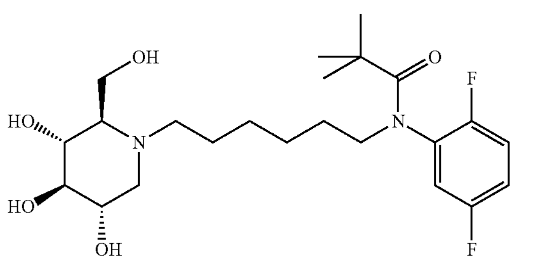 [SMILES: CC(C)(C)C(=O)N(CCCCCCN1C[C@H](O)[C@@H](O)[C@H](O)[C@H]1CO)c1cc(F)ccc1F] | 0.4 | 18 | >500 |
| 7 | 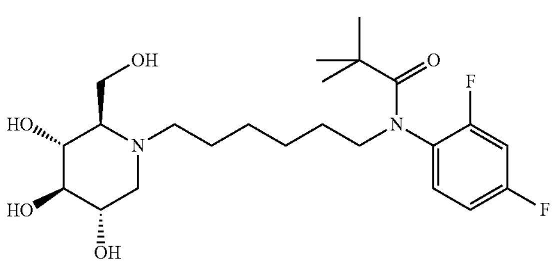 [SMILES: CC(C)(C)C(=O)N(CCCCCCN1C[C@H](O)[C@@H](O)[C@H](O)[C@H]1CO)c1ccc(F)cc1F] | 0.25 | 45 | >500 |
| 8 | 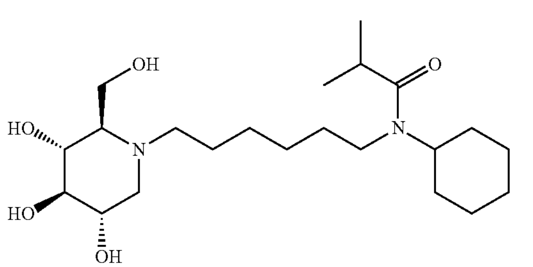 [SMILES: CC(C)C(=O)N(CCCCCCN1C[C@H](O)[C@@H](O)[C@H](O)[C@H]1CO)C1CCCCC1] | 0.45 | 25 | >500 |
| 9 | 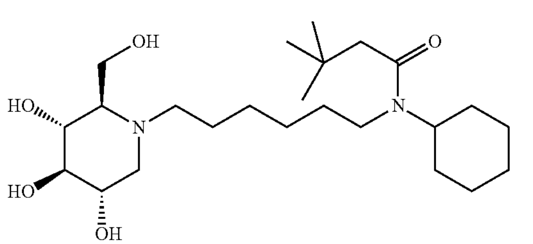 [SMILES: CC(C)(C)CC(=O)N(CCCCCCN1C[C@H](O)[C@@H](O)[C@H](O)[C@H]1CO)C1CCCCC1] | 0.18 | 4 | >500 |

TABLE 3-continued

Examples of Alkylated Imino Sugar Compounds and their Potencies for Biological Activity

| Entry | Structure | BVDV EC$_{50}$ | BVDV EC$_{90}$ | CC$_{50}$ |
|---|---|---|---|---|
| 10 | 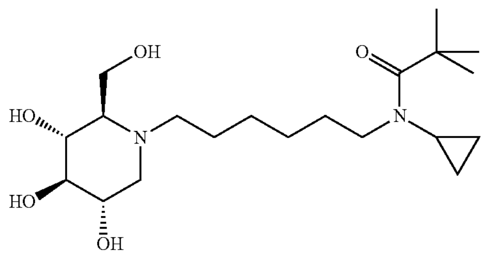 [SMILES: CC(C)(C)C(=O)N(CCCCCCN1C[C@H](O)[C@@H](O)[C@H](O)[C@H]1CO)C1CC1] | 3.75 | 100 | >500 |
| 11 | 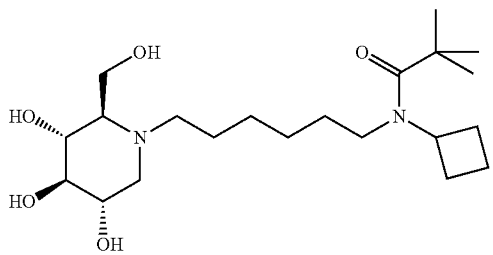 [SMILES: CC(C)(C)C(=O)N(CCCCCCN1C[C@H](O)[C@@H](O)[C@H](O)[C@H]1CO)C1CCC1] | 0.8 | 100 | >500 |
| 12 | 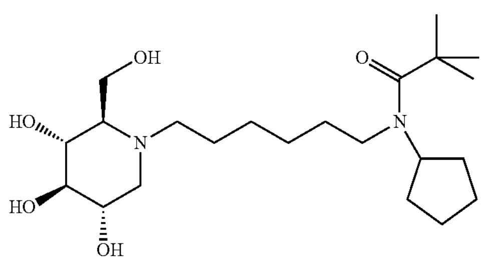 [SMILES: CC(C)(C)C(=O)N(CCCCCCN1C[C@H](O)[C@@H](O)[C@H](O)[C@H]1CO)C1CCCC1] | 0.85 | 32 | >500 |
| 13 | 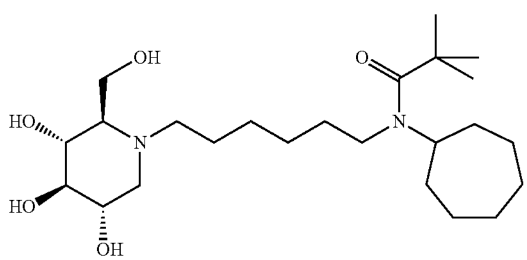 [SMILES: CC(C)(C)C(=O)N(CCCCCCN1C[C@H](O)[C@@H](O)[C@H](O)[C@H]1CO)C1CCCCCC1] | 0.4 | 9 | >500 |
| 14 | 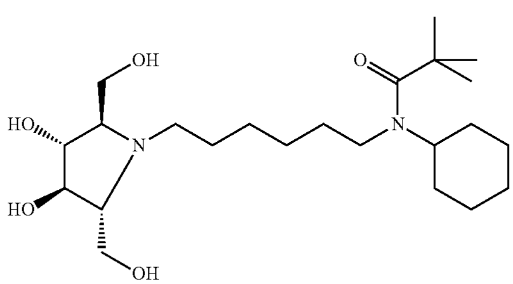 [SMILES: CC(C)(C)C(=O)N(CCCCCCN1[C@H](CO)[C@@H](O)[C@H](O)[C@H]1CO)C1CCCCC1] | 21 | 100 | >500 |

TABLE 3-continued

Examples of Alkylated Imino Sugar Compounds and their Potencies for Biological Activity

| Entry | Structure | BVDV EC$_{50}$ | BVDV EC$_{90}$ | CC$_{50}$ |
|---|---|---|---|---|
| 15 | 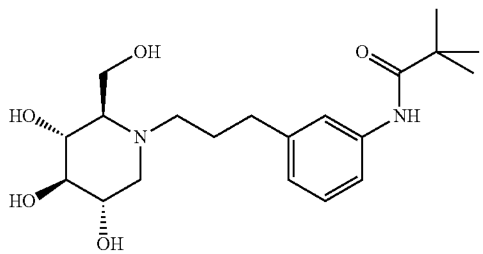 [SMILES: CC(C)(C)C(=O)Nc1cccc(CCCN2C[C@H](O)[C@@H](O)[C@H](O)[C@H]2CO)c1] | 2.4 | 100 | >500 |
| 16 | 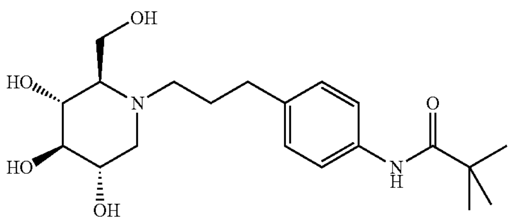 [SMILES: CC(C)(C)C(=O)Nc1ccc(CCCN2C[C@H](O)[C@@H](O)[C@H](O)[C@H]2CO)cc1] | >100 | | >500 |
| 17 | 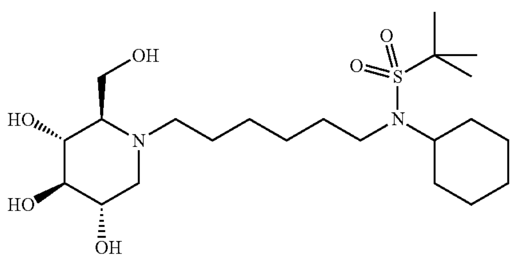 [SMILES: CC(C)(C)S(=O)(=O)N(CCCCCCN1C[C@H](O)[C@@H](O)[C@H](O)[C@H]1CO)C1CCCCC1] | 0.31 | 50 | >500 |
| 18 | 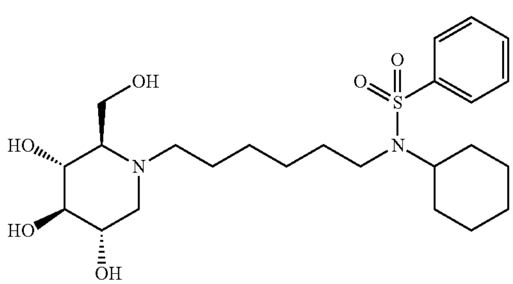 [SMILES: O=S(=O)(c1ccccc1)N(CCCCCCN1C[C@H](O)[C@@H](O)[C@H](O)[C@H]1CO)C1CCCCC1] | 0.5 | 18 | 200 |
| 19 | 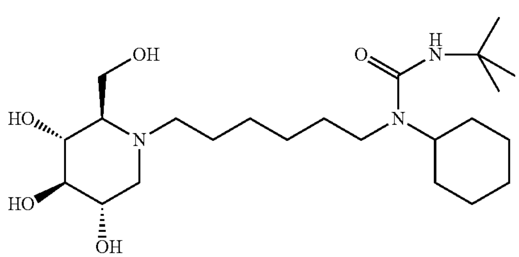 [SMILES: CC(C)(C)NC(=O)N(CCCCCCN1C[C@H](O)[C@@H](O)[C@H](O)[C@H]1CO)C1CCCCC1] | 0.3 | 25 | >500 |

TABLE 3-continued

Examples of Alkylated Imino Sugar Compounds and their Potencies for Biological Activity

| Entry | Structure | BVDV EC$_{50}$ | BVDV EC$_{90}$ | CC$_{50}$ |
|---|---|---|---|---|
| 20 | 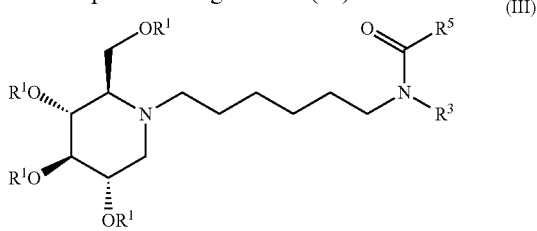 | 0.32 | 11 | >500 |

What is claimed is:

1. The compound having formula (III):

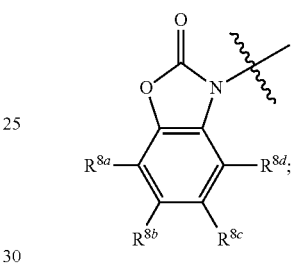
(III)

Including hydrates, solvates, pharmaceutically acceptable salts, and complexes thereof, wherein:

$R^1$ at each occurrence is independently selected from the group consisting of hydrogen and $COR^4$;

$R^5$ is selected from a group consisting of optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, optionally substituted aryl which may be substituted by 0-5 moieties, $OR^{5'}$ and $NHR^6$;

$R^3$ is selected from a group consisting of optionally substituted $C_{1-6}$ alkyl, optionally substituted branched $C_{1-6}$ alkyl, optionally substituted cyclic $C_{3-8}$ alkyl, 1-adamantyl, 2-adamantyl, optionally substituted $C_5$-$C_{10}$ bicycloalkyl, and optionally substituted aryl which may be substituted by 0-5 moieties;

$R^3$ and $R^5$ are taken together with the atom to which they are bound to form an optionally substituted ring having 5 ring atoms;

$R^3$ and $R^5$ are taken together with the atom to which they are bound to form an optionally substituted ring having 5 ring atoms;

$R^3$ and $R^5$ are taken together with the atom to which they are bound to form

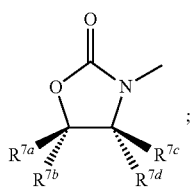

$R^3$ and $R^5$ are taken together with the atom to which they are bound to form

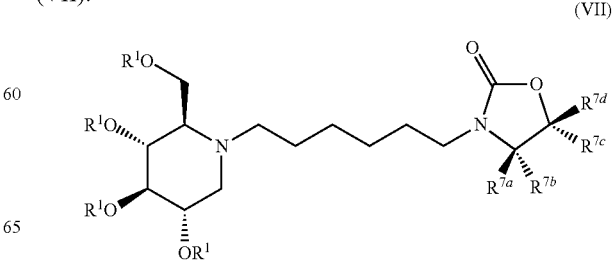

$R^4$ at each occurrence is independently selected from the group consisting of optionally substituted $C_{1-6}$ alkyl and optionally substituted branched $C_{1-6}$ alkyl;

$R^5$ is selected from a group consisting of an optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

$R^6$ is selected from a group consisting of hydrogen, an optionally substituted $C_{1-6}$ alkyl, optionally substituted branched $C_{1-6}$ alkyl, optionally substituted cyclic $C_{3-8}$ alkyl, optionally substituted $C_5$-$C_{10}$ bicycloalkyl, and optionally substituted aryl which may be substituted by 0-5 moieties;

$R^{7a}$, $R^{7b}$, $R^{7c}$, and $R^{7d}$ are each selected from a group consisting of hydrogen, optionally substituted $C_{1-6}$ alkyl, and optionally substituted aryl which may be substituted by 0-5 moieties;

$R^{8a}$, $R^{8b}$, $R^{8c}$, and $R^{8d}$ are each selected from a group consisting of hydrogen, halogen, optionally substituted $C_{1-6}$ alkyl, optionally substituted branched $C_{1-6}$ alkyl, and optionally substituted $C_{1-6}$ alkoxy.

2. The compound according to claim 1 having formula (VII):

(VII)

Including hydrates, solvates, pharmaceutically acceptable salts, prodrugs and complexes thereof.

3. The compound according to claim 1 having formula (VIII):

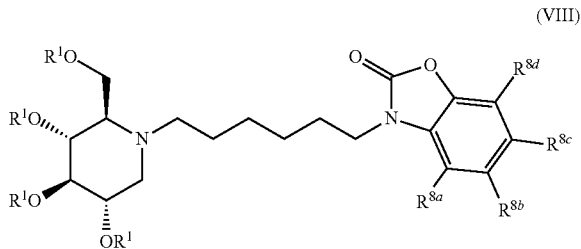

(VIII)

Including hydrates, solvates, pharmaceutically acceptable salts, prodrugs and complexes thereof.

4. The compound according to claim 1 that is:
N-cyclohexyl-N-(6-((2R,3R,4R,5S)-3,4,5-trihydroxy-2-(hydroxymethyl) piperidin-1-yl)hexyl)benzamide;
(2R,3R,4R,5S)-2-((butyryloxy)methyl)-1-(6-(N-cyclohexylpivalamido) hexyl)piperidine-3,4,5-triyl tributyrate;
tert-butyl(2-methylcyclohexyl)(6-((2R,3R,4R,5S)-3,4,5-trihydroxy-2-(hydroxymethyl)piperidin-1-yl)hexyl) carbamate;
(2R,3R,4R,5S)-2-(hydroxymethyl)-1-(6-((2-ethylcyclohexyl)amino) hexyl)piperidine-3,4,5-triol;
N-(2-methylcyclohexyl)-N-(6-((2R,3R,4R,5S)-3,4,5-trihydroxy-2-(hydroxymethyl)piperidin-1-yl)hexyl)pivalamide;
N-cyclohexyl-N-(6-((2R,3R,4R,5S)-3,4,5-trihydroxy-2-(hydroxymethyl) piperidin-1-yl)hexyl)acetamide;
tert-butyl (6-((2R,3R,4R,5S)-3,4,5-trihydroxy-2-(hydroxymethyl)piperidin-1-yl)hexyl)carbamate;
N-cyclohexyl-N-(6-((2R,3R,4R,5S)-3,4,5-trihydroxy-2-(hydroxymethyl) piperidin-1-yl)hexyl)pivalamide;
N-(2,5-difluorophenyl)-N-(6-((2R,3R,4R,5S)-3,4,5-trihydroxy-2-(hydroxyl methyl)piperidin-1-yl)hexyl)acetamide;
N-(2,4-difluorophenyl)-N-(6-((2R,3R,4R,5S)-3,4,5-trihydroxy-2-(hydroxyl methyl)piperidin-1-yl)hexyl)acetamide;
N-(2,5-difluorophenyl)-N-(6-((2R,3R,4R,5S)-3,4,5-trihydroxy-2-(hydroxyl methyl)piperidin-1-yl)hexyl)pivalamide;
N-(2,4-difluorophenyl)-N-(6-((2R,3R,4R,5S)-3,4,5-trihydroxy-2-(hydroxyl methyl)piperidin-1-yl)hexyl)pivalamide;
N-cyclohexyl-N-(6-((2R,3R,4R,5S)-3,4,5-trihydroxy-2-(hydroxymethyl) piperidin-1-yl)hexyl)isobutyramide;
N-cyclohexyl-3,3-dimethyl-N-(6-((2R,3R,4R,5S)-3,4,5-trihydroxy-2-(hydroxymethyl)piperidin-1-yl)hexyl)butanamide;
N-cyclopropyl-N-(6-((2R,3R,4R,5S)-3,4,5-trihydroxy-2-(hydroxyl methyl)piperidin-1-yl)hexyl)pivalamide;
N-cyclobutyl-N-(6-((2R,3R,4R,5S)-3,4,5-trihydroxy-2-(hydroxymethyl) piperidin-1-yl)hexyl)pivalamide;
N-cyclopentyl-N-(6-((2R,3R,4R,5S)-3,4,5-trihydroxy-2-(hydroxymethyl) piperidin-1-yl)hexyl)pivalamide;
N-cycloheptyl-N-(6-((2R,3R,4R,5S)-3,4,5-trihydroxy-2-(hydroxymethyl) piperidin-1-yl)hexyl)pivalamide;
N-cyclooctyl-N-(6-((2R,3R,4R,5S)-3,4,5-trihydroxy-2-(hydroxymethyl) piperidin-1-yl)hexyl)pivalamide;
N-((1R,5R,7S)-adamantan-2-yl)-N-(6-((2R,3R,4R,5S)-3,4,5-trihydroxy-2-(hydroxymethyl)piperidin-1-yl)hexyl)pivalamide;
N-((3S,5S,7S)-adamantan-1-yl)-N-(6-((2R,3R,4R,5S)-3,4,5-trihydroxy-2-(hydroxymethyl)piperidin-1-yl)hexyl)pivalamide;
(S)-4-phenyl-3-(6-((2R,3R,4R,5S)-3,4,5-trihydroxy-2-(hydroxymethyl) piperidin-1-yl)hexyl)oxazolidin-2-one;
(R)-4-phenyl-3-(6-((2R,3R,4R,5S)-3,4,5-trihydroxy-2-(hydroxymethyl) piperidin-1-yl)hexyl)oxazolidin-2-one;
3-(6-((2R,3R,4R,5S)-3,4,5-trihydroxy-2-(hydroxymethyl)piperidin-1-yl)hexyl)benzo[d]oxazol-2(3H)-one;
1-cyclohexyl-3-phenyl-1-(6-((2R,3R,4R,5S)-3,4,5-trihydroxy-2-(hydroxyl methyl)piperidin-1-yl)hexyl)urea;
1-cyclohexyl-1-(6-((2R,3R,4R,5S)-3,4,5-trihydroxy-2-(hydroxymethyl) piperidin-1-yl)hexyl)urea;
N-cyclohexyl-N-(6-((2R,3R,4R,5S)-3,4,5-trihydroxy-2-(hydroxymethyl) piperidin-1-yl)hexyl)benzamide;
1-cyclohexyl-3-propyl-1-(6-((2R,3R,4R,5S)-3,4,5-trihydroxy-2-(hydroxymethyl)piperidin-1-yl)hexyl)urea;
(2R,3R,4R,5S)-2-(acetoxymethyl)-1-(6-(N-cyclohexylpivalamido) hexyl)piperidine-3,4,5-triyl triacetate;
(2R,3R,4R,5S)-2-((butyryloxy)methyl)-1-(6-(N-cyclohexylmethyl sulfonamido)hexyl)piperidine-3,4,5-triyl-tributyrate;
(2R,3R,4R,5S)-2-(acetoxymethyl)-1-(6-(N-cyclohexylmethylsulfonamido) hexyl)piperidine-3,4,5-triyl triacetate;
(2R,3R,4R,5S)-1-(6-(dicyclohexylamino)hexyl)-2-(hydroxymethyl) piperidine-3,4,5-triol;
N-(3-(3-((2R,3R,4R,5S)-3,4,5-trihydroxy-2-(hydroxymethyl)piperidin-1-yl)propyl)phenyl)pivalamide;
N-(4-(3-((2R,3R,4R,5S)-3,4,5-trihydroxy-2-(hydroxymethyl)piperidin-1-yl)propyl)phenyl)pivalamide;
3-(tert-butyl)-1-cyclohexyl-1-(6-((2R,3R,4R,5S)-3,4,5-trihydroxy-2-(hydroxymethyl)piperidin-1-yl)hexyl) urea;
N-cyclohexyl-2,4-difluoro-N-(6-((2R,3R,4R,5S)-3,4,5-trihydroxy-2-(hydroxymethyl)piperidin-1-yl)hexyl) benzamide;
N-cyclohexyl-2,4,5-trifluoro-N-(6-((2R,3R,4R,5S)-3,4,5-trihydroxy-2-(hydroxymethyl)piperidin-1-yl)hexyl) benzamide;
or a pharmaceutically acceptable form thereof.

5. A composition comprising an effective amount of at least one compound according to claim 1.

6. The composition according to claim 5, further comprising at least one excipient.

7. The composition according to claim 6, wherein the at least one compound is at least one member selected from the group consisting of:
N-cyclohexyl-N-(6-((2R,3R,4R,5S)-3,4,5-trihydroxy-2-(hydroxymethyl) piperidin-1-yl)hexyl)benzamide;
(2R,3R,4R,5S)-2-((butyryloxy)methyl)-1-(6-(N-cyclohexylpivalamido) hexyl)piperidine-3,4,5-triyl tributyrate;
tert-butyl(2-methylcyclohexyl)(6-((2R,3R,4R,5S)-3,4,5-trihydroxy-2-(hydroxymethyl)piperidin-1-yl)hexyl) carbamate;
(2R,3R,4R,5S)-2-(hydroxymethyl)-1-(6-((2-ethylcyclohexyl)amino) hexyl)piperidine-3,4,5-triol;
N-(2-methylcyclohexyl)-N-(6-((2R,3R,4R,5S)-3,4,5-trihydroxy-2-(hydroxymethyl)piperidin-1-yl)hexyl)pivalamide;

N-cyclohexyl-N-(6-((2R,3R,4R,5S)-3,4,5-trihydroxy-2-(hydroxymethyl) piperidin-1-yl)hexyl)acetamide;
tert-butyl (6-((2R,3R,4R,5S)-3,4,5-trihydroxy-2-(hydroxymethyl)piperidin-1-yl)hexyl)carbamate;
N-cyclohexyl-N-(6-((2R,3R,4R,5S)-3,4,5-trihydroxy-2-(hydroxymethyl) piperidin-1-yl)hexyl)pivalamide;
N-(2,5-difluorophenyl)-N-(6-((2R,3R,4R,5S)-3,4,5-trihydroxy-2-(hydroxyl methyl)piperidin-1-yl)hexyl)acetamide;
N-(2,4-difluorophenyl)-N-(6-((2R,3R,4R,5S)-3,4,5-trihydroxy-2-(hydroxyl methyl)piperidin-1-yl)hexyl)acetamide;
N-(2,5-difluorophenyl)-N-(6-((2R,3R,4R,5S)-3,4,5-trihydroxy-2-(hydroxyl methyl)piperidin-1-yl)hexyl)pivalamide;
N-(2,4-difluorophenyl)-N-(6-((2R,3R,4R,5S)-3,4,5-trihydroxy-2-(hydroxyl methyl)piperidin-1-yl)hexyl)pivalamide;
N-cyclohexyl-N-(6-((2R,3R,4R,5S)-3,4,5-trihydroxy-2-(hydroxymethyl) piperidin-1-yl)hexyl)isobutyramide;
N-cyclohexyl-3,3-dimethyl-N-(6-((2R,3R,4R,5S)-3,4,5-trihydroxy-2-(hydroxymethyl)piperidin-1-yl)hexyl)butanamide;
N-cyclopropyl-N-(6-((2R,3R,4R,5S)-3,4,5-trihydroxy-2-(hydroxyl methyl)piperidin-1-yl)hexyl)pivalamide;
N-cyclobutyl-N-(6-((2R,3R,4R,5S)-3,4,5-trihydroxy-2-(hydroxymethyl) piperidin-1-yl)hexyl)pivalamide;
N-cyclopentyl-N-(6-((2R,3R,4R,5S)-3,4,5-trihydroxy-2-(hydroxymethyl) piperidin-1-yl)hexyl)pivalamide;
N-cycloheptyl-N-(6-((2R,3R,4R,5S)-3,4,5-trihydroxy-2-(hydroxymethyl) piperidin-1-yl)hexyl)pivalamide;
N-cyclooctyl-N-(6-((2R,3R,4R,5S)-3,4,5-trihydroxy-2-(hydroxymethyl) piperidin-1-yl)hexyl)pivalamide;
N-((1R,5R,7S)-adamantan-2-yl)-N-(6-((2R,3R,4R,5S)-3,4,5-trihydroxy-2-(hydroxymethyl)piperidin-1-yl)hexyl)pivalamide;
N-((3S,5S,7S)-adamantan-1-yl)-N-(6-((2R,3R,4R,5S)-3,4,5-trihydroxy-2-(hydroxymethyl)piperidin-1-yl)hexyl)pivalamide;
(S)-4-phenyl-3-(6-((2R,3R,4R,5S)-3,4,5-trihydroxy-2-(hydroxymethyl) piperidin-1-yl)hexyl)oxazolidin-2-one;
(R)-4-phenyl-3-(6-((2R,3R,4R,5S)-3,4,5-trihydroxy-2-(hydroxymethyl) piperidin-1-yl)hexyl)oxazolidin-2-one;
3-(6-((2R,3R,4R,5S)-3,4,5-trihydroxy-2-(hydroxymethyl)piperidin-1-yl)hexyl)benzo[d]oxazol-2(3H)-one;
1-cyclohexyl-3-phenyl-1-(6-((2R,3R,4R,5S)-3,4,5-trihydroxy-2-(hydroxyl methyl)piperidin-1-yl)hexyl)urea;
1-cyclohexyl-1-(6-((2R,3R,4R,5S)-3,4,5-trihydroxy-2-(hydroxymethyl) piperidin-1-yl)hexyl)urea;
N-cyclohexyl-N-(6-((2R,3R,4R,5S)-3,4,5-trihydroxy-2-(hydroxymethyl) piperidin-1-yl)hexyl)benzamide;
1-cyclohexyl-3-propyl-1-(6-((2R,3R,4R,5S)-3,4,5-trihydroxy-2-(hydroxymethyl)piperidin-1-yl)hexyl)urea;
(2R,3R,4R,5S)-2-(acetoxymethyl)-1-(6-(N-cyclohexylpivalamido) hexyl)piperidine-3,4,5-triyl triacetate;
(2R,3R,4R,5S)-2-((butyryloxy)methyl)-1-(6-(N-cyclohexylmethyl sulfonamido)hexyl)piperidine-3,4,5-triyl tributyrate;
(2R,3R,4R,5S)-2-(acetoxymethyl)-1-(6-(N-cyclohexylmethylsulfonamido) hexyl)piperidine-3,4,5-triyl triacetate;
(2R,3R,4R,5S)-1-(6-(dicyclohexylamino)hexyl)-2-(hydroxymethyl) piperidine-3,4,5-triol;
N-(3-(3-((2R,3R,4R,5S)-3,4,5-trihydroxy-2-(hydroxymethyl)piperidin-1-yl)propyl)phenyl)pivalamide;
N-(4-(3-((2R,3R,4R,5S)-3,4,5-trihydroxy-2-(hydroxymethyl)piperidin-1-yl)propyl)phenyl)pivalamide;
3-(tert-butyl)-1-cyclohexyl-1-(6-((2R,3R,4R,5S)-3,4,5-trihydroxy-2-(hydroxymethyl)piperidin-1-yl)hexyl)urea;
N-cyclohexyl-2,4-difluoro-N-(6-((2R,3R,4R,5S)-3,4,5-trihydroxy-2-(hydroxymethyl)piperidin-1-yl)hexyl)benzamide;
N-cyclohexyl-2,4,5-trifluoro-N-(6-((2R,3R,4R,5S)-3,4,5-trihydroxy-2-(hydroxymethyl)piperidin-1-yl)hexyl)benzamide;
or a pharmaceutically acceptable form thereof.

* * * * *